United States Patent [19]

Conaway et al.

[11] Patent Number: 5,792,634

[45] Date of Patent: Aug. 11, 1998

[54] RNA POLYMERASE TRANSCRIPTION FACTOR

[75] Inventors: Ronald Charles Conaway; Joan Weliky Conaway, both of Oklahoma City, Okla.; John N. Bradsher, New York, N.Y.

[73] Assignee: Oklahoma Medical Research Foundation, Oklahoma City, Okla.

[21] Appl. No.: 524,757

[22] Filed: Sep. 7, 1995

Related U.S. Application Data

[63] Continuation-in-part of PCT/US94/13621 Nov. 29, 1994, which is a continuation-in-part of Ser. No. 160,087, Nov. 30, 1993, abandoned.

[51] Int. Cl.$^6$ .............................. C12N 9/00; C07K 14/47
[52] U.S. Cl. .............................. 435/183; 530/350
[58] Field of Search .............................. 530/350; 435/183

[56] References Cited

PUBLICATIONS

Ngo et al., The protein Folding Problem and Tertiaky Structure Prediction, 1994, Mertz et al. (ed.) Birkhauser, Boston, MA, pp. 433 and 492–495.

Bengal et al., "Role of mammalian transcription factors IIF, IIS, and IIX during elongation by RNA polymerase II," Mol Cell Biol 11:1195–1206(1991).

Bradsher et al., "RNA polymerase II transcription factor SIII," J Biol Chem 268:25587–25593 (1993).

Buratowski, S. "DNA repair and transcription: the helicase connection," Science 260:37–38 (1993).

Chafin et al. "Identification and purification of a yeast protein that affects elongation by RNA polmerase, II," J Biol Chem 266:9256–9262 (1991).

Conaway et al., "Transcription factor SIII: a novel component of the RNA polymerase, II elongation complex," Cell Mol Biol Res 39:323–329 (1993).

Garrett, et al., "Molecular cloning of an essential subunit of RNA polymerase II elongation factor SIII," Proc Natl Acad Sci USA 91:5237–5241 (1994).

Gerard et al., "Purification and interaction properties of the human RNA polymerase B(II) general transcription factor BRF2," J Biol Chem 266:20940–20945 (1991).

Krauskopf et al., "The block to transcription elongation at the minute virus of mice attenuator is regulated by cellular elongation factors," Mol Cell Biol 11:3515–3521 (1991).

Madore et al., "Genetic analysis of the cofactor requirement for human immunodeficiency virus type I Tat function," J Virology 67:3703–3711 (1993).

Natori et al., "DNA dependent RNA polymerase from Ehrlich ascites tumor cells," J Biochem 73:879–888 (1973).

Rosen, C.A., "HIV regulator proteins: potential targets for therapeutic intervention," AIDS Research and Human Retroviruses 8:175–181 (1992).

Schaeffer et al., "DNA repair helicase: a component of BTF2 (TFIIH) basic transcription factor," Science 260:58–63 (1993).

Sekimizu et al., "Purification of a factor from Ehrlich ascites tumor cells specifically stimulating RNA polmerase, II," Biochemistry 15:5064–5070 (1976).

Wright, S., "Regulation of eukaryotic gene expression by transcriptional attenuation," Molecular Biology of the Cell 4:661–668 (1993).

*Primary Examiner*—George C. Elliott
*Assistant Examiner*—Terry A. McKelvey
*Attorney, Agent, or Firm*—Sidley & Austin

[57] ABSTRACT

A new RNA polymerase transcription factor has been discovered. The enzyme significantly increases the rate of transcription elongation by RNA polymerase II.

8 Claims, 2 Drawing Sheets

RNA POLYMERASE TRANSCRIPTION FACTOR

RELATED APPLICATION

This is a continuation-in-part of application Ser. No. PCT/US94/13621 filed Nov. 29, 1994, which is a continuation-in-part of U.S. application Ser. No. 08/160,087 filed Nov. 30, 1993, now abandoned.

GOVERNMENT RIGHTS

The invention described herein was made in the course of work under a grant or award from The National Institutes of Health, and the Government may have certain rights therein.

TECHNICAL FIELD

This invention relates to the field of RNA polymerase transcription factors.

BACKGROUND OF THE INVENTION

Transcription is the first stage in gene expression and the principal step at which it is controlled. It involves synthesis of an RNA chain representing the coding strand of a DNA duplex. Transcription takes place by the usual process of complementary base pairing catalyzed by the enzyme RNA polymerase. This reaction can be divided into three stages: initiation; elongation; and termination.

In eucaryotic systems, RNA polymerase associates with several other enzymes and factors at a sequence of DNA which defines a promoter. Accurate initiation requires a number of initiation factors and is an important point at which transcription is controlled.

Elongation describes the phase during which the RNA polymerase moves along the DNA and extends the growing RNA chain. As the RNA polymerase moves, it unwinds the DNA helix to expose a new segment of the template in single-stranded form. Nucleotides are covalently added to the 3' end of the growing RNA chain forming an RNA-DNA hybrid in the unwound region. Additionally, the RNA that was made previously is displaced from the DNA template strand, which pairs with its original partner to reform the duplex helix. Thus, elongation involves the disruption of DNA structure to form a transiently unwound region that exists as a hybrid RNA-DNA duplex and a displaced single strand of DNA.

Termination involves recognition by the RNA polymerase of the point at which no further bases should be added to the chain, followed by dissociation of RNA polymerase from both the DNA template and the newly synthesized RNA chain.

Messenger RNA synthesis is a complex biochemical process requiring the action of multiple transcription factors, including initiation and elongation factors, that control the activity of the RNA polymerase at both the initiation and elongation stages of transcription. Several of these factors are known to be essential for initiation and are referred to as factors d, e, a, g, and b from *Saccharomyces cerevisiae*, τ, α, βγ, δ and ε from rat liver, and TFIID, TFIIB, RAP30/74 or TFIIF, BTF2 or TFIIH, and TFIIE from human cells.

In addition to these factors, other proteins have been shown to stimulate either the initiation or elongation stages of transcription by RNA polymerase II. One such factor, designated TFIIA, has been purified from both *Saccharomyces cerevisiae* and mammalian cells and appears to promote assembly of the preinitiation complex. Although TFIIA is not essential for initiation, several lines of evidence suggest that it functions to increase the number of productive preinitiation complexes formed at a variety of promoters in vitro.

Although considerable progress has recently been achieved identifying and characterizing transcription factors that support a basal level of transcription by RNA polymerase II, significantly less information is available on transcription factors that control the efficiency of transcription initiation or RNA chain elongation. Such activities play an important role in regulating gene expression.

Only two transcription factors that influence RNA chain elongation have been identified and characterized with a high degree of certainty. The general initiation factor TFIIF (PAP 30/74) from Drosophila and human cells has been shown to stimulate the rate of RNA chain elongation and to promote read-through by RNA polymerase at a variety of pause sites. Transcription factor SII has been shown to promote RNA polymerase read-through at intrinsic pause sites in a human histone gene, in the adenovirus genome, and at several other sites.

A transcription factor designated YES was recently purified to apparent homogeneity from *Saccharomnyces cerevisiae*. YES is composed of a single 115 kDa polypeptide and appears to stimulate the rate of RNA chain elongation by RNA polymerase on synthetic oligo(dC)-tailed DNA templates, although its existence is now in question. Additionally, a transcription factor designated TFIIX has been described. However, it has not yet been purified; thus, it is not yet clear how it is related to other better characterized elongation factors.

Many of the initiation factors and one or more elongation factors (e.g., TFIIF) are commercially available from most suppliers of biological enzymes (e.g., Upstate Biotechnology, Promega Corp., and Santa Cruz Biotechnology, Inc.). The ability of RNA polymerase to form an active complex in vitro capable of specifically initiating and efficiently elongating RNA is vital to the development of genetically engineered industrial systems for the production of recombinant products. Furthermore, other as yet unknown elongation factors hold the key to many cellular functions. Thus, the ability to manipulate the transcription of genes is necessary to overcome many hurdles in genetic engineering and will be required to cure several human diseases.

One such area which relies upon elucidation of genetic mechanisms is the effort to understand the etiology and treatment of diseases caused by viruses. For example, one of the most intensive efforts in recent years has focused on the HIV virus which causes Acquired Immune Deficiency Syndrome (AIDS). It has been reported that the HIV encoded Tat protein recruits unknown cofactors to the HIV-1 LTR TAR element (Madore, et al., *J Virology* 67: 3703 (1993)) thereby inducing activation of viral gene expression. There is reason to believe the unknown co-factors are likely to be elongation factors, and thus, further identification of elongation factors are important in elucidating genetic means for treating AIDS. In addition, as the HIV Tat protein is itself believed to be an elongation factor, cellular elongation factors will be important components of assay systems designed to identify pharmacologic agents that interfere with the activity of the HIV Tat protein. (Rosen, C. A., *AIDS Research and Human Retroviruses* 8: 175–181 (1992)).

Elongation factors are also believed to be involved with the repair of actively transcribed genes. Transcribed genes are repaired on a priority basis because the resulting translation product would likely be either a mutated full-length product or a truncated product (due to premature termination of transcription). Elongation factors would be a likely signal for repair systems such as ERCC 3 because they are one of the few enzymes which are associated with DNA only when mRNA is actually being elongated. Elucidation of this signal could result in a treatment for certain repair deficiency diseases such as xeroderma pigmentosum and Cockaynes syndrome.

Elongation factors are also likely to be involved in the regulation of a number of cellular genes including the proto oncogene C-myc and genes involved in the cellular stress response.

In brief, the presence or absence of these elongation factors controls the rate of transcription of many genes and their absence can even prevent continued transcription. They are certainly involved in the coordination of transcription with other cellular functions. However, despite the advances made to date in the field of genetic engineering, there is a continuing need for novel factors which affect the rate and efficiency of transcription.

SUMMARY OF THE INVENTION

A novel RNA polymerase transcription factor, designated Elongin or SIII, is provided. Increasing the available amount of this protein in transcription systems significantly increases the rate of transcription.

In another embodiment the present invention is directed to a method for isolating Elongin from eukarotic cells. For example, brain and liver cells can be used as sources of this novel transcription factor.

In another embodiment, the present invention is directed toward the cDNAs encoding both the rat and human Elongin subunits of ~15, ~18 and ~110 kDa.

In still another embodiment the present invention is directed toward recombinantly produced Elongin as well as the vectors and transformation systems which make that possible.

These and other features, aspects and advantages of the present invention will become better understood with reference to the following description and appended claims.

DETAILED DESCRIPTION

Figure 1:
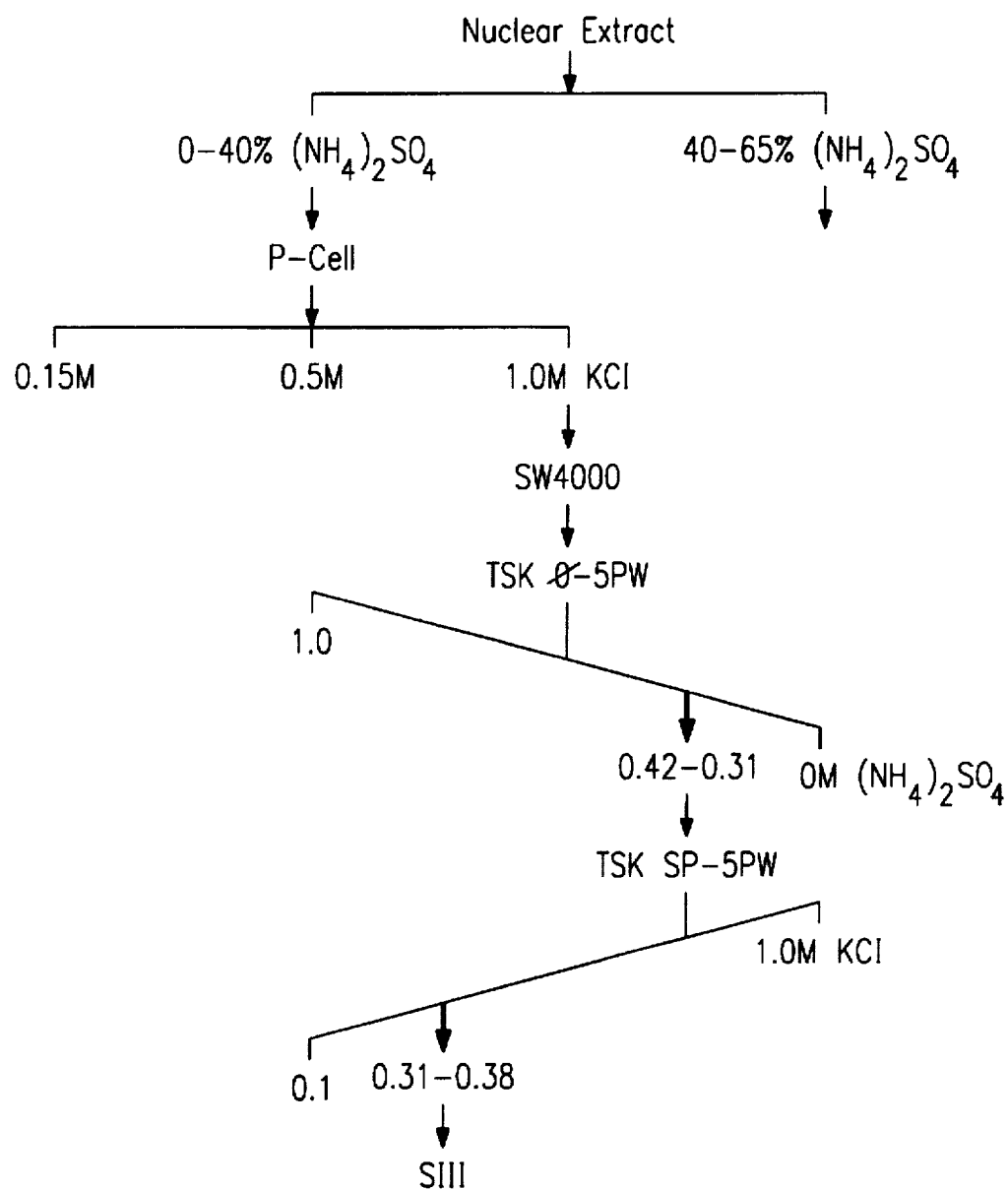
FIG. 1 is a preferred purification scheme of RNA polymerase transcription factor SIII (Elongin) from rat liver, where P-cell represents phosphocellulose and $\phi$ represents a phenyl group.

The following description provides details of the manner in which the embodiments of the present invention may be made and used in order to achieve the separation, purification and characterization of an RNA polymerase elongation factor (Elongin) which was not previously known. Also included is a description for the recombinant production of this factor. These descriptions, while exemplary of the present invention, are not to be construed as specifically limiting the invention, and such variations which would be within the purview of one skilled in this art are to be considered to fall within the scope of this invention.

Definitions

The abbreviations used are: AMP-PNP, adenyl-5'-yl imidodiphosphate; PMSF, phenylmethylsulfonyl fluoride; TFA, trifluoroacetic acid; HPLC, high pressure liquid chromatography; DTT, dithiothreitol; HEPES, N-[2-hydroxyethyl] piperazine-N'-[2-ethanesulfonic acid]; SDS, sodium dodecyl sulfate; EDTA, ethylenediaminetetraacetic acid; AdML, adenovirus 2 major late; USF, upstream stimulatory factor; and MLTF, major late transcription factor. "~" means approximately. Whenever a nucleic acid is referred to, either directly or inferentially, it may be meant to include the nucleic acid in both the sense and anti-sense orientations.

A new RNA polymerase transcription factor has now been isolated. This transcription factor can be used to increase the rate of transcription by stimulating synthesis by RNA polymerase. Several lines of evidence demonstrate that this transcription factor, designated Elongin or SIII, is a heterotrimeric protein composed of approximately 110, 18, and 15 kDa subunits. These are: (i) polypeptides of approximately 110, 18, and 15 kDa compose at least about 90% of the protein in the most highly purified preparations of Elongin; (ii) Elongin activity co-chromatographs with approximately 110, 18, and 15 kDa polypeptides during both ion-exchange and hydrophobic interaction HPLC; (iii) Elongin activity can be reconstituted by recombining the approximately 110, 18, and 15 kDa polypeptides isolated by reverse phase HPLC; and (iv) based on the results of gel filtration and sedimentation experiments, Elongin exhibits a native molecular mass of about 140 kDa, consistent with the idea that it contains a single copy of each of the three polypeptides.

Elongin is structurally distinct from the TATA factor (τ/TFIID), its DNA binding subunit (the TATA Binding Protein or TBP), and general initiation factors α(TFIIB), βγ(TFIIF), δ(BTF2/TFIIH), and ε(TFIIE). Nor will it replace any of these factors in reconstitution of promoter-specific initiation. In addition, its polypeptide composition differs from that of TFIIA which stimulates transcription initiation by RNA polymerase. Elongin also appears to be distinct from elongation factors designated SII and TFIIX. Mammalian SII is composed of a single, 38 kDa polypeptide, and thus differs structurally from Elongin. TFIIX, on the other hand, has thus far been defined only as an activity present in a chromatographic fraction from HeLa cells. However, while both Elongin and the TFIIX activity bind tightly to phosphocellulose and are eluted between 0.5 and 1.0M KCl, Elongin flows through DEAE cellulose at 0.1M KCl (data not shown), while TFIIX binds this resin and is eluted between 0.1 and 0.5M KCl.

The following examples describe experiments investigating the functional properties of Elongin. These indicate that Elongin stimulates promoter specific transcription by increasing the rate of RNA chain elongation by RNA polymerase. The following observations argue that Elongin exerts its activity directly on the elongation complex: (i) in pulse chase experiments, Elongin does not need to be present during preinitiation complex formation or transcription initiation in order to stimulate transcription; and (ii) Elongin stimulates the rate of RNA chain elongation during transcription of double stranded oligo dC-tailed templates. In this respect, the activity of Elongin resembles that of the well-characterized transcription elongation factor SII and the elongation stimulatory activity of TFIIF.

By several criteria, the functional properties of Elongin more closely resemble those of TFIIF than those of SII. SII has been shown to suppress RNA polymerase pausing in response to intrinsic signals found in a variety of genes, including the human histone H3.3, the Adenovirus major late, and murine adenosine deaminase genes, but it does not appear to produce a general increase in the rate of RNA chain elongation. In contrast, TFIIF does not release polymerase paused at intrinsic pause sites, but it is reported to increase the rate of RNA chain elongation. Under appropriate reaction conditions, RNA polymerase can achieve "physiological," elongation rates of 1200–1500 nt/mmn in the presence of the TFIIF factor.

Like TFIIF, Elongin is capable of stimulating the overall rate of RNA chain elongation under a variety of experimental conditions. In the presence of 500 μM NTPs and either Elongin or recombinant βγ (TFIIF), RNA polymerase elongates RNA chains at about 500 nucleotides/min, consistent with previously reported rates of TFIIF-stimulated elongation measured at 30° C. Elongin is capable of strongly stimulating the rate of elongation of promoter-specific transcripts in the presence of βγ(TFIIF) concentrations that just saturate the initiation reaction.

Present data also indicates that Elongin does not promote read-through by polymerase paused at the intrinsic H3.3 pause site. In addition, unlike SII, Elongin does not promote cleavage of nascent RNA molecules by paused or stalled RNA polymerase. SII and Elongin, therefore, are members of different classes of transcription elongation factors and may perform complementary functions in the regulation of eukaryotic messenger RNA synthesis.

In summary, RNA polymerase transcription factor SIII (Elongin) is defined as a protein, which is composed of subunits with electrophoretic mobilities corresponding to relative molecular masses of ~110 kDa (Elongin A), ~18 kDa (Elongin B) and ~15 kDa (Elongin C) and which is capable of increasing the rate at which purified RNA polymerase incorporates ribonucleoside triphosphates into RNA chains.

All steps in the purification of Elongin are preferably carried out in buffer maintained at about pH 6.5–8.5 unless otherwise indicated.

Elongin was purified from a crude nuclear fraction from rat liver, although Elongin can be present in any nucleated cell. This crude nuclear fraction contains, in addition to Elongin, a large amount of contaminating DNA and RNA as well as many other proteins and enzymes. The procedure summarized below allows separation of Elongin from these contaminants. The purified Elongin represents <~0.001% (by weight of protein) of the starting material.

Because many nuclear proteins are bound tightly to nucleic acid or other insoluble nuclear components at low ionic strength, in one embodiment of acquiring Elongin, nuclei were extracted with a moderate concentration of ammonium sulfate $(NH_4)_2 SO_4$ to solubilize as much nuclear protein as possible. Insoluble material was typically removed by centrifugation at >20,000×g, although other methods known to one skilled in the art can be used.

Ammonium sulfate precipitation was used as the preferred initial fractionation step. Following ammonium sulfate fractionation, Elongin activity was present in a fraction of protein that was insoluble in about 40% is ammonium sulfate. This protein fraction was further fractionated by cation exchange chromatography. Fractions containing Elongin activity were pooled, and the Elongin further purified using gel exclusion chromatography, or any other procedure which separates proteins according to molecular size. Active fractions from gel exclusion chromatography were pooled and preferably applied to a hydrophobic interaction chromatography resin. The hydrophobic interaction chromatography resin was eluted with a descending concentration gradient of ammonium sulfate. Active fractions were pooled and preferably applied to a cation exchange resin. Active fractions prepared using this or a similar combination of fractionation steps (the order is not necessarily critical) contained three major polypeptides with electrophoretic mobilities corresponding to relative molecular masses of ~110 kDa, ~18 kDa, and 15 kDa.

These three polypeptides were further purified and separated from one another by reverse phase HPLC. Prior to reverse phase HPLC, the protein was denatured in a solution containing urea, guanidine hydrochloride, trifluoroacetic acid, and acetonitrile. This procedure allowed clean separation of the three polypeptides, which each eluted as a single, sharp peak. When the Elongin fraction was loaded onto the reverse phase column without prior denaturation with urea and guanidine hydrochloride, Elongin A eluted from the column in multiple broad peaks, which most likely represent different conformers of the polypeptide.

Following reverse phase separation of the three Elongin polypeptides, they were mixed together and renatured in various combinations. To renature the Elongin polypeptides, volatile solvents from reverse phase fractionation were removed by lyophilization. Dried protein was dissolved in a high concentration of the chaotropic agent guanidine hydrochloride and then rapidly diluted in a pH 7.9 "refolding" buffer containing a moderate concentration of salt, a reducing agent, glycerol, and a low concentration of $ZnSO_4$, which may promote proper folding of one or more of the Elongin polypeptides. To remove guanidine hydrochloride, the protein solution was dialyzed for several hours against refolding buffer.

After carrying out the above protocol, various combinations of the renatured Elongin A, B and C polypeptides were assayed for their abilities to stimulate transcription elongation by RNA polymerase II. The results of this experiment indicated that all three polypeptides are required for full activity of Elongin.

Elongin can also be acquired through the utilization of genetic engineering techniques. The methods required to develop an expression system from an isolated protein are known in the art. (Old and Primrose, *Principles of Gene Manipulation*, 4th. ed. (1989) and Sambrook et al., *Molecular Cloning*, 2ed., Cold Spring Harbor Laboratory Press, (1989) both of which are incorporated herein by reference).

The cDNAs for the rat derived Elongin C, B and A subunits have been sequenced (SEQ ID NO: 1, SEQ ID NO: 3, and SEQ ID NO: 5, respectively) as well as the amino acid sequences deduced from those cDNA sequences (SEQ ID NO: 2, SEQ ID NO: 4, and SEQ ID NO: 6, respectively). The methods used are described in Example 2 and are standard procedures in the art. For isolation of cDNAs encoding Elongin C and Elongin B, sense and antisense nucleotide sequences based on tryptic peptides of particular subunits were used as primers for PCR. The PCR products were then subcloned to produce plasmid vectors containing partial cDNA sequences. Those cDNAs encoding the complete subunits were obtained by screening rat cDNA libraries using radioactive probes derived from these plasmid vectors by asymmetric PCR. For isolation of cDNAs encoding the Elongin A, a rat cDNA library was screened with degenerate oligonucleotides encoding Elongin A tryptic peptide sequences to identify candidate cDNAs. Bona fide Elongin A cDNA clones were identified by PCR screening, using a primer whose sequence was based on an Elongin A tryptic peptide sequence. Although these methods worked for their intended purposes, numerous variations which will occur to one skilled in the art, are possible to achieve the same result.

The individual subunits were then produced with M13 expression vectors as described in Example 3. Any of the known expression methods would be suitable substitutions for this vector system, including eukaryotic systems such as baculovirus. The three subunits can then be recombined into the quaternary structure with the expected activity (See Example 4).

Example 5 details the methods used to obtain the cDNA for the human Elongin C subunit (SEQ ID NO: 7; amino acid sequence, SEQ ID NO: 8), the human Elongin B subunit (SEQ ID NO: 9; amino acid sequence, SEQ ID NO: 10) and the human Elongin A subunit (SEQ ID NO: 11; amino acid sequence SEQ ID NO: 12). Briefly probes were prepared from the corresponding rat subunit cDNAs. These probes were then used in PCR or other methods to obtain the human sequences from either a human peripheral blood lymphocyte or human umbilical vein endothelial cell cDNA library. Again, there are various ways known to one skilled in the art to obtain this end. As Elongin cDNA has now been found in human peripheral blood lymphocyte, human umbilical vein endothelial cell, rat brain and rat liver cDNA libraries, it is expected that Elongin is a ubiquitous protein, involved with transcription in most cells. Therefore, it is expected that Elongin cDNA can be isolated from many other mammalian cDNA libraries.

In one embodiment of the invention, probes are made corresponding to sequences of the cDNAs which are complimentary to the mRNA for Elongin. These probes can be radioactively or non-radioactively labeled in a number of ways well known to those skilled in the art for use in screening for Elongin related proteins or diagnostics. The probes can be made of various lengths. Factors such as stringency and GC content may influence the desired probe length for a particular application. Generally, they can be from 10 nucleotides to the entire nucleic acid coding for a given subunit.

EXAMPLE 1

Isolation, Purification and Detection of Elongin
(See FIG. 1 and Table I)

Materials

Male Sprague-Dawley rats (200–300 gm) were purchased from SASCO. Unlabelled ultra pure ribonucleoside 5'-triphosphates and DATP were from Pharmacia LKB Biotechnology, Inc. (Piscataway, N.J.). AMP-PNP was obtained from Sigma Chemical Co. (St. Louis, Mo.) or Pharmacia. [$\alpha$-$^{32}$P] CTP (>650 Ci/mmol) and [$\alpha$-$^{32}$P] ATP (>650 Ci/mmol) were obtained from ICN Biomedicals, Inc. (Costa Mesa, Calif.). PMSF, antipain, and heparin were from Sigma Chemical Co. Leupeptin was obtained from Boehringer Mannheim Corp. (Indianapolis, Ind.). Bovine serum albumin (Pentex fraction V) was obtained from ICN ImmunoBiologicals. Glycerol (spectranalyzed grade) was from Fisher Scientific (Pittsburgh, Pa.). Schwarz/Mann ultrapure sucrose and ammonium sulfate were from ICN Biomedicals, Inc. For reverse-phase chromatography, acetonitrile and trifluoroacetic acid (HPLC/Spectro grade) and urea and guanidine hydrochloride (Sequanal grade) were from Pierce (Rockford, Ill.).

Chromatography and Buffers

Phosphocellulose (P11) and DEAE-cellulose (DE51) were purchased from Whatman, Inc. (Clifton, N.J.). 4000SW Spherogel TSK, Spherogel TSK phenyl-5-PW, and Spherogel TSK SP5-PW were obtained from Beckman Instruments, Inc. (Fullerton, Calif.). HPLC was performed using a Beckman System Gold chromatograph. Buffer A was 20 mM HEPES-NaOH, pH 7.9, 1 mM EDTA, 1 mM DTT, 20% (v/v) glycerol, and 0.5 mM PMSF. Buffer B was 50 mM Tris-HCl, pH 7.9, 0.1 mM EDTA, 1 mM DTT, 20% (v/v) glycerol, and 0.5 mM PMSF. Buffer D was 40 mM HEPES-NaOH, pH 7.9, 0.5 mM EDTA, 1 mM DTT, and 10% (v/v) glycerol. Buffer E was 40 mM HEPES-NaOH, pH 7.9, 0.1 mM EDTA, 1 mM DTT, and 10% (v/v) glycerol. Buffer G was 40 mM HEPES-NaOH, pH 7.0, 0.5 mM EDTA, 1 mM DTT, and 10% (v/v) glycerol.

Purification of Elongin

Step 1. Preparation of the Nuclear Extract. A 0.33M $(NH_4)_2SO_4$ extract of crude rat liver nuclei was prepared from the livers of 300 male Sprague-Dawley rats as previously described (Conaway, J. W. and Conaway, R. C., *J Biol Chem* 264: 2357–2362 (1989)). All further operations were carried out at 4° C.

Step 2: $(NH_4)_2SO_4$ Fractionation. Solid $(NH_4)_2SO_4$ (0.186 g/ml) was added slowly to the nuclear extract. After addition of 1 µl 1.0N NaOH per gram of $(NH_4)_2SO_4$, the suspension was stirred an additional 30 min. The precipitate was collected by centrifugation at 12,000×g for 45 min and then dissolved in Buffer B containing antipain and leupeptin at 10 µg/ml each (Fraction I).

Step 3: DEAE-cellulose (DE52) Chromatography. Fraction I was diluted with Buffer B to a conductivity equivalent to that of 0.1M $(NH_4)_2SO_4$ in Buffer B and then centrifuged at 7,500×g for 15 min. The supernatant was mixed with 1.0 liter of DEAE-cellulose pre-equilibrated with Buffer B containing 0.1M $(NH_4)_2SO_4$ in a 10.5-cm diameter column. The slurry was allowed to sit for 45 min with occasional stirring and then filtered at 1.0 liter/hour. The column was washed at the same flow rate with Buffer B containing 0.1M $(NH_4)_2SO_4$ until the eluate contained <0.05 mg/ml protein. Fractions containing protein were pooled and dialyzed against Buffer A to a conductivity equivalent to that of 0.1M KCl in Buffer A (Fraction II).

Step 4: Phosphocellulose (P11) Chromatography. Fraction II was centrifuged at 4,000×g for 10 min, and the supernatant was mixed with 800 ml of phosphocellulose pre-equilibrated with Buffer A containing 0.15M KCl in a 10.5-cm diameter column. The slurry was allowed to sit for 45 min with occasional stirring and then filtered at 500 ml/hour. The column was washed at the same flow rate with Buffer A containing 0.5M KCl until the eluate contained less than 0.05 mg/ml protein. Transcription activity was eluted stepwise at one packed column volume/hour with Buffer A containing 1.0M KCl. Fractions of one-fifth column volume were collected, and those containing activity were pooled and dialyzed against Buffer A containing 0.5M $(NH_4)_2SO_4$ for 2.5 hours (Fraction III).

Step 5: TSK 4000SW HPLC. Solid $(NH_4)_2SO_4$ (0.3 g/ml) was added slowly to Fraction III with stirring. 1 µl of 1.0N NaOH per gram of $(NH_4)_2SO_4$ was then added, and the suspension was stirred an additional 30 min. The precipitate was collected by centrifugation at 15,000×g for 90 min and dissolved to a final volume of 5 ml in Buffer G. The solution was dialyzed against Buffer G until the conductivity was equivalent to that of Buffer G in 0.5M $(NH_4)_2SO_4$ and then centrifuged at 80,000×g for 20 min. The resulting supernatant was applied to a 4000SW Spherogel TSK HPLC column (21.5×600 mm) pre-equilibrated in Buffer G in 0.5M KCl. The column was eluted at 4 ml/min and 5 ml fractions were collected. Active fractions were pooled (Fraction IV).

Step 6: TSK Phenyl-5-PW HPLC. Fraction IV was diluted with an equal volume of Buffer E containing 2.0M $(NH_4)_2SO_4$, and then centrifuged at 60,000×g for 20 min. The resulting supernatant was applied to a Spherogel TSK phenyl-5PW column (21.5×150 mm) pre-equilibrated in Buffer E containing 1.0M $(NH_4)_2SO_4$. Transcription activity was eluted at 5 ml/min with a 500 ml linear gradient from 1.0M $(NH_4)_2SO_4$ in Buffer E to Buffer E. Ten ml fractions were collected, and the active fractions, which eluted between 0.45 to 0.3M $(NH_4)_2SO_4$, were pooled and dialyzed against Buffer D containing 0.05M KCl to a conductivity equivalent to that of Buffer D in 0.1M KCl (Fraction V).

Step 7: TSK SP-5-PW HPLC. Fraction V was centrifuged at 60.000×g for 20 min, and the supernatant was applied to a Spherogel TSK SP-5-PW column (7.5×75 mm) pre-equilibrated in Buffer D containing 0.1M KCl. The column was eluted at 1 ml/min with a 50 ml linear gradient from 0.1 to 0.8M KCl in Buffer D. One ml fractions were collected. Transcription activity eluted between 0.31 and 0.38M KCl (Fraction VI).

Preparation of RNA Polymerase II and Transcription Factors

RNA polymerase II (Serizawa, et al., *Proc Natl Acad Sci USA* 89: 7476–7480 (1992)) the native rat TATA factor τ (Conaway et al., *J Biol Chem* 265: 7552–7558 (1990)) and transcription factor δ (BTF2) (Conaway, R. C. and Conaway, J. W., *Proc Natl Acad Sci USA* 86: 7356–7360 (1989); and Conaway, et al., *J Biol Chem* 267: 10142–10148 (1992)) were purified from rat liver as previously described. Recombinant yeast TFIID was expressed and purified as described (Conaway, et al., *J Biol Chem* 266: 7804–7811 (1991)) from bacterial strain N5151 containing the plasmid pASY2D (Schmidt, et al., *Proc Natl Acad Sci USA* 86: 7785–7789 (1989)). Recombinant rat α (TFIIB) (Tsuboi, et al., *Nucleic Acids Res* 20: 3250 (1992)) and recombinant human TFIIE (Peterson, et al., *Nature* 354: 369–373 (1991))

TABLE I

Purification of transcription factor Elongin from rat liver

| FRACTION | PROTEIN (mg) | VOLUME (ml) | ACTIVITY[a] (units) | SPECIFIC ACTIVITY (units/mg) | YIELD (%) |
|---|---|---|---|---|---|
| I. Nuclear Extract 40% $(NH_4)_2SO_4$ fraction | 25,000 | | | | |
| II. DEAE Cellulose (DE-52) | 13,000 | 3550 | | | |
| III. Phosphocellulose (P-11) | 240 | 400 | 445,000 | 1,850 | 100[b] |
| IV. TSK-SW4000 | 70 | 35 | 287,000 | 4,100 | 65 |
| V. TSK-phenyl-5PW | 4.2 | 60 | 56,300 | 13,400 | 13 |
| VI. TSK-SP-5PW | 0.35 | 6 | 182,000 | 519,000 | 41 |

[a] Runoff transcription assays performed as described on page 23 using the Eco RI to Nde I fragment from pDN-AdML DNA as template. Following a 30 minute preincubation of RNA polymerase II, transcription factors, and DNA, runoff transcription was carried out for an additional 18 min in the presence of 50 μM ATP, 2 μM UTP, 10 μM CTP, 50 μM GTP, and 10 μCi [α-$^{32}$P] CTP. One unit is the amount of Elongin required to reconstitute half maximal runoff transcription.
[b] Overall yield is based on fraction III since Elongin activity could not be reliably measured in fractions I and II.

Purification of Elongin Polypeptide by Reverse Phase Chromatography

Reverse phase narrow bore HPLC was performed using an Ultra-fast Micro Protein Analyzer (Michrom BioResources, Pleasanton, Calif.). An aliquot (~50 μg) of Elongin (Fraction VI) was diluted 1:1 with "magic mix", (Nugent, et al., *J Chromatography* 443: 381–397 (1988)), denaturant (4.0M guanidine hydrochloride, 4.0M urea, 7.5% acetonitrile, 0.15% TFA), and 0.2% Zwittergent ZC-8 (Calbiochem) and applied to a 2.1×50 mm PLRP-S (1000 Å pore size; 8μ particle size) reverse phase HPLC column (Michrom BioResources) pre-equilibrated at 54° C. in 20% eluent B (90% acetonitrile, 0.09% TFA, and 0.03% Zwittergent ZC-8) and 80% eluent A (2% acetonitrile, 0.1% TFA, and 0.03% Zwittergent ZC-8). The column was developed at 0.4 ml/min with a 22 min linear gradient from 20% to 75% eluent B. Peaks of absorbance at 220 nm were collected manually.

Recovery of Elongin Activity Following Reverse Phase HPLC

Fractions from reverse phase narrow bore HPLC were lyophilized until just dry using a Savant Speed-Vac (Savant Instruments, Farmingdale, N.Y.). Dried protein was resuspended in 5 μl of 6.0M guanidine hydrochloride and left on ice for 30 min. Aliquots were then diluted to 50 μl with renaturation buffer (40 mM HEPES-NaOH, pH 7.9, 0.1M KCl, 2 mM DTT, 50 μM $ZnSO_4$, 0.1 mM EDTA, and 10% (v/v) glycerol) and left on ice an additional 90 min. Aliquots were then dialyzed for 2 hours against renaturation buffer lacking EDTA and DTT and stored at −80° C.

were prepared as described, except that the 56 kDa subunit of TFIIE was expressed in BL21(DE3). Recombinant βγ (TFIIF) was purified by phosphocellulose chromatography (Conaway, J. W. and Conaway, R. C., *J Biol Chem* 264: 2357–2362 (1989)) of whole cell extracts prepared from SF21 cells co-infected with recombinant baculoviruses encoding the βγ (TFIIF) subunits, human RAP74 (Aso, et al., *Nature* 355: 461–464 (1992); and Finkelstein, et al., *Nature* 355: 464–467 (1992)) and rat RAP30 (Garrett, et al., *J Biol Chem* 267: 23942–23949 (1992)). Recombinant viruses were constructed using the BacPAK6 baculovirus expression system (Clontech Laboratories, Inc., Palo Alto, Calif.).

Assay of Runoff Transcription

Unless indicated otherwise, preinitiation complexes were assembled as described (Conaway, et al., *J Biol Chem* 262: 8293–8297 (1987)) by preincubation of 100 ng of Nde I-digested pDN-AdML, (Conaway R. C. and Conaway, J. W., *J Biol Chem* 263: 2962–2968 (1988)) or 100 ng of Nde I-digested $pN_4$ (Lorch, et al., *Cell* 49: 203–210 (1987)) and approximately 10 ng of recombinant α (TFIIB), 10 ng of recombinant βγ(TFIIF), 7 ng of recombinant human TFIIE, 40 ng of δ (BTF2) (Fraction VI), 60 ng τ (Fraction V) or 50 ng of recombinant yeast TFIID (AcA 44 fraction), and 0.01 unit of RNA polymerase II. Transcription was initiated by addition of 7 mM $MgCl_2$ and 50 μM ATP, 2 μM UTP, 10 μM CTP, 50 μM GTP and 10 μCi [α-$^{32}$P] CTP. After incubation at 28° C. for 18 min runoff transcripts were analyzed by electrophoresis through 6% polyacrylamide/7.0M urea gels. Transcription was quantitated by densitometry of autoradiograms using an LKB UltroScan XL laser densitometer.

Sucrose Gradient Sedimentation

Sedimentation was performed in 2 ml linear sucrose gradients (15–30% [v/v] containing 20 mM HEPES-NaOH, pH 7.9, 1 mM EDTA, 1 mM DTT, and 0.4M KCl). Centrifugation was carried out at 55,000 rpm and 4° C. in the TLS55 rotor of a Beckman TL100 ultracentrifuge. Fractions (2 drops) were collected from the bottom of tubes through a 20-gauge needle.

Protein Determination

Protein concentrations were determined using the protein dye assay (Bio-Rad Laboratories, Hercules, Calif.) with bovine serum albumin as the standard.

Detection of Elongin

Elongin-dependent transcriptional stimulation is readily detected if any of the four ribonucleoside triphosphates are present at limiting concentrations. This property of Elongin was exploited to purify it to apparent homogeneity from rat liver nuclear extracts. Elongin was assayed by its ability to reconstitute synthesis of a 250-nucleotide runoff transcript from the core region of the AdML promoter in the presence of a limiting concentration of UTP and saturating amounts of RNA polymerase II, initiation factors α(TFIIB), βγ(TFIIF), δ(BTF2/TFIIH), and ε(TFIIE), and either the native rat TATA factor τ or recombinant yeast TFIID. The standard template was pDN-AdML (Conaway, R. C. and Conaway, J. W., $J$ $Biol$ $Chem$ 263: 2962–2968 (1988)), which includes AdML core promoter sequences, but which lacks the upstream sequences that mediate stimulation of transcription by USF/MLTF.

Elongin was purified to near homogeneity from a 0.33M $(NH_4)_2SO_4$ extract of crude rat liver nuclei by ammonium sulfate fractionation, followed by chromatography on successive DEAE-cellulose, phosphocellulose, TSK 4000SW, TSK phenyl-5-PW, and TSK SP-5-PW columns. Elongin activity was first reliably measured in the phosphocellulose fraction (Fraction III). Approximately 350 μg of Elongin (Fraction VI) can be purified from ~3 kg of rat liver. The overall yield from Fraction III was approximately 40%. The more than 100% yield of Elongin activity on TSK SP-5-PW was most likely due to removal of inhibitors present in Fraction V.

Elongin is a multi-subunit protein composed of ~110, ~18, and ~15 kDa polypeptides, Elongin A, B and C, respectively. Analysis of the TSK SP-5-PW column fractions by SDS-polyacrylamide gel electrophoresis revealed that polypeptides with apparent molecular masses of approximately 110, 18, and 15 kDa co-chromatographed with transcriptional stimulatory activity and accounted for more than 90% of the protein in the active fractions. Transcriptional stimulatory activity did not elute from TSK SP-5-PW in a symmetrical peak. The bulk of activity was recovered in fractions 25 and 26, but significant activity eluted as a shoulder on the leading edge of this peak. The two small polypeptides appeared to be present in higher molar amounts (relative to the large polypeptide) in fractions 25 and 26 than in the earlier eluting fractions. In addition, it was observed that the Elongin subunits also co-chromatographed with transcriptional activity when Elongin was analyzed by hydrophobic interaction chromatography on TSK phenyl-5-PW (data not shown).

To determine which polypeptides were required to reconstitute Elongin activity, the protein in an aliquot of fraction 26 from the TSK SP-5-PW column was denatured and fractionated by reverse phase HPLC. The Elongin subunits were each recovered in apparently homogeneous form. The polypeptides were renatured alone or in combination with other polypeptides and assayed for activity. Transcriptional activity was recovered only when all three polypeptides were combined and renatured together. It could not be reconstituted with any single polypeptide renatured independently or with any combination of independently renatured polypeptides. In addition, transcriptional activity could not be recovered when pairs of polypeptides were renatured together. However, in studies using recombinant subunits (See Example 4) a slight stimulation of transcription was observed with Elongin A alone; the combination of Elongin A and Elongin C had somewhat more activity and maximal activity depended on the presence of Elongin A, B and C. Thus, it appears that Elongin A alone exhibits a low, basal level of transcription while both the Elongin B and Elongin C strongly stimulate this activity.

As measured by TSK 4000SW size exclusion HPLC, Elongin has a Stokes radius of ~47 Å. By sucrose gradient sedimentation, Elongin has a sedimentation coefficient of ~6 S. Assuming a partial specific volume of 0.725 ml/g, Elongin has an apparent native molecular mass determined by the method of Siegel and Monty (Siegel, L. M. and Monty, K. J., $Biochim$ $Biophys$ $Acta$ 112: 346–362 (1966)) of ~140 kDa, consistent with Elongin being a heterotrimer composed of a single copy each of the ~110, ~18, and ~15 kDa polypeptides.

EXAMPLE 2

Isolation of cDNA Clones Encoding Rat Elongin
Method for Generating cDNA From ~15 kDa Elongin Subunit—Elongin C Approximately 300 pmol of Elongin C, isolated by reverse phase HPLC, was digested with trypsin. The $NH_2$ terminal sequences of four tryptic peptides (I–IV), determined by automated Edman microsequencing, were as follows: I, $NH_2$-LISSDGHEFIVKR-COOH (SEQ ID NO:13);II, $NH_2$-AMLSGPGQFAENETNEVNFR-COOH (SEQ ID NO:14); III, $NH_2$-VCMYFTYK-COOH (SEQ ID NO:15);IV, $NH_2$-YTNSSTEIPEFPIAPEIALELLMAANFLD-COOH (SEQ ID NO:16). A partial cDNA encoding residues 51-97 of the Elongin C was isolated by polymerase chain reaction (PCR) using as primers the sense and antisense degenerate oligonucleotides 5'-CARTTYGCNGARAAYGARAC-3' (SEQ ID NO:17) and 5'-GGNGCDATNGGRAAYTCNGG-3' (SEQ ID NO:18) encoding residues 8 through 14 of tryptic peptide II and residues 9 through 15 of tryptic peptide IV, respectively. PCR was performed for 30 cycles of 1 min at 94° C., 1 min at 46° C., and 2 min at 72° C. with 1.5 mM $MgCl_2$, 0.25 mM dNTPs, 2.5 units of Taq polymerase, 0.02 $A_{260}$ unit of each primer, and ~6×10$^6$ pfu of a rat liver λgt11 cDNA library (Clontech). PCR products encoding Elongin C polypeptide sequences were identified by Southern blotting, using as probe the 5'-$^{32}$P-labeled degenerate oligonucleotide 5'-ACNAAYGARGTNAAYTTYMG-3' (SEQ ID NO:19), which encodes residues 14 through 20 of tryptic peptide II, isolated by preparative polyacrylamide gel electrophoresis, and subcloned by blunt end ligation into pBluescript KS(–). Bacteria harboring a recombinant plasmid (pKG1) carrying the partial Elongin C cDNA were identified by colony hybridization using the same 5'-$^{32}$P-labeled degenerate oligonucleotide as probe. cDNAs encoding the complete Elongin C polypeptide were obtained by screening rat liver and rat brain λ ZAP II cDNA libraries (Stratagene, La Jolla, Calif.) with an internally labeled, single stranded DNA probe synthesized by asymmetric PCR, using pKG1 as template. pBluescript SK(–) phagemids containing cDNA inserts were rescued with helper phage and sequenced by the dideoxy chain termination method using a Sequenase kit (United States Biochemical Corp., Cleveland, Ohio). Two overlapping clones were combined to generate the full length rat Elongin C coding sequence (SEQ ID NO:1, nucleotide sequence; SEQ ID NO:2, amino acid sequence).

Method for Generating cDNA From ~18 kDa Elongin Subunit—Elongin B

Approximately 300 pmol of Elongin B was isolated by reverse phase HPLC (Bradsher, et al., *J Biol Chem* 268: 25587–25593 (1993a)). After reduction, S-carboxyamidomethylation, and digestion with trypsin, the resultant mixture was further fractionated by microbore HPLC. Optimal peptides were determined by differential UV absorbance and matrix-assisted laser desorption mass spectrometry (Lasermat; Finnigan-MAT, San Jose, Calif.) and submitted to automated Edman microsequencing (Lane, et al., *J Prot Chem* 10: 151–160 (1991)). The N-terminal sequences of two tryptic peptides (I and II) were obtained and were as follows: I. LYKDDQLLDDGKTLGECGFTSQTARPQ(A)(P) (SEQ ID NO:20) and II. ADDTGEALRIEPFSSPPELPDVMKPQDSG[G] (S)AN [E] (SEQ ID NO:21). A partial Elongin B cDNA was isolated from a rat liver λgt11 cDNA library (Clontech) by PCR, using as primers the sense and antisense degenerate oligonucleotides 5'-TNTA(Y)AA(R)GA(Y)GA(Y)CA(R)(Y)T-3' (SEQ ID NO:22) and 5'-TGNGG(Y)TTCATNAC (R)TCNGG-3' (SEQ ID NO:23), which encode portions of tryptic peptide I and tryptic peptide II, respectively (R is A or G; Y is C or T; N is A, C, G, or T). PCR was performed for 30 cycles of 1 min at 94° C., 1 min at 46° C., and 2 min at 72° C. with 1.5 mM MgCl$_2$, 0.25 mM dNTPs, 2.5 units of Taq polymerase, and 0.02 A$_{260}$ unit of each primer. PCR products encoding Elongin B polypeptide sequences were identified by Southern blotting using as probe the 5'-$^{32}$P-labeled degenerate oligonucleotide 5'-GCNGA(Y)GA(Y) ACNTT(Y)GA(R)GC-3' (SEQ ID NO:24) which encodes residues 1–7 of tryptic peptide I, isolated by preparative polyacrylamide gel electrophoresis and subcloned by blunt-end ligation into pBluescript KS(-). Bacteria harboring the recombinant plasmid (pKG2) carrying the partial Elongin B CDNA were identified by colony hybridization using the same 5'-$^{32}$P-labeled degenerate oligonucleotide as probe. A CDNA encoding the complete Elongin B polypeptide was obtained by screening a rat brain XZAP II cDNA library (Stratagene, La Jolla, Calif.) with an internally labeled, single-stranded DNA probe synthesized by asymmetric PCR (McCabe, P.C., PCR Protocols: *A Guide to Methods and Applications*. Innis, et al., eds. (San Diego: Academic Press), pp. 76–83 (1990)) using pKG2 as template. Bluescript SK(-) phagemids containing cDNA inserts were rescued with VCS-M13 interference-resistant helper phage (Stratagene) and sequenced by the dideoxy chain-termination method using a Sequenase kit (United States Biochemical Corp.). The Elongin B nucleotide sequence is given in SEQ ID NO:3, and the corresponding amino acid sequence is listed in SEQ ID NO:4.

Method for Generating cDNA From ~110 kDA Elongin Subunit—Elongin A

Approximately 300 pmol of Elongin A was isolated by reverse phase HPLC (Bradsher, et al., *J Biol Chem* 268: 25587–25593 (1993)). After reduction, S-carboxyamidomethylation, and digestion with trypsin, the resultant mixture was further fractionated by microbore HPLC. Optimal peptides were determined by differential UV absorbance and matrix-assisted laser desorption mass spectrometry (Lasermat; Finnigan-MAT, San Jose, Calif.), and then submitted to automated Edman microsequencing, (Lane, et al., *J Prot Chem* 10: 151–160 (1991)). The NH$_2$ terminal sequence of two trypyic peptides (I and II) were as follows: I. DVPQQEEEAEGNYQESWQASGSQPY(Y)(P)EHR (SEQ ID NO:25); II. ANENKSDKLQPAGAEP-TRP (SEQ ID NO:26). Two oligonucleotide "guessmer" probes were designed according to human codon usage bias. At some positions, inosine (I), was used instead of a mixture of four nucleotides. Primer 1, which is the complement of a sequence encoding amino acids 1–15 of tryptic peptide I, was 5'TCCTGGTAGTTICCTCIG CCTCCTCCTCCTGCT-GIGGIACGTC (SEQ ID NO:27), and Primer 2, which is the complement of a sequence encoding amino acids 10–17 of tryptic peptide two, was 5'CGGATCGTIGG(T/C) TCIGCICCIGCIGG(T/C)TG (SEQ ID NO:28).

A λGEM2 library constructed from size selected (>2 kb) cDNA derived from rat brain (from Dr. Roger Wiegand, Monsanto Corp., Saint Louis, Mo.) was screened with 5'-$^{32}$P-labeled Primer 1. Hybridization was at 37° C. for 20 hours in 6× standard saline citrate (SSC)/1+ Denhardt's solution/0.05% sodium pyrophosphate containing denatured salmon testes DNA at 100 μg/ml. Sixty-nine clones were isolated from 5×10$^5$ plaques. Phage clones derived from oligonucleotide screening were further screened by the polymerase chain reaction (PCR) method, using a T7 primer, CGTAATACGACTCACTATAGGG, (SEQ ID NO:29), which hybridizes to a sequence in the λGEM2 vector, and Primer 2, respectively, as sense and anti-sense primers. PCR reactions were performed for 30 cycles of 1 min at 94° C., 1 min at 55° C., and 2 min at 72° C. PCR reactions performed with eight of 69 phage clones yielded discrete products; the clone yielding the largest PCR product was selected and sequenced by the dideoxy chain termination method using a Sequenase kit. The Elongin A nucleotide sequence is given in SEQ ID NO:5 and the corresponding amino acid sequence is listed in SEQ ID NO:6.

EXAMPLE 3

Expression of Rat Elongin in *E. Coli*

Expression of Elongin C in *E. coli*

Overexpression of Elongin C in *E. coli* was accomplished using an M13mpET bacteriophage expression system. The entire Elongin C coding sequence was introduced into M13mpET, which contains the complete pET T7 transcription/expression region. A 100-ml culture of *E. coli* strain JM109(DE3) (Promega) was grown to an OD$_{600}$ of 0.6 in SOB medium containing 2.5 mM MgCl$_2$ at 37° C. with gentle shaking. Cells were infected with M13mpET carrying the full-length Elongin C cDNA at a multiplicity of infection of 10–20. After an additional 2 hours at 37° C., cells were induced with 0.4 mM isopropyl β-D-thiogalactoside, and the culture was incubated an additional 2.5 hours. Cells were harvested by centrifugation at 2000×g for 10 min at 4° C., and inclusion bodies were prepared as previously described (Lin, K. & Cheng, S. *BioTechniques* 11: 748–753 (1991)), except that DNase and RNAse treatments were omitted. Inclusion bodies were solubilized by resuspension in 2 ml of ice-cold 50 mM Tris-HCl (pH 8.0) containing 6M guanidine hydrochloride. The resulting suspension was clarified by centrifugation at 50,000×g for 20 min at 4° C.

Expression of Histidine-tagged Elongin B in *E. coli*

Overexpression of histidine-tagged Elongin B was accomplished using an M13mpET bacteriophage expression system (Tan, et al., *BioTechniques* 16: 824–828 (1994)). To make the expression vector m13mpET-6Hpl8, which encodes pl8 with an 10 amino acid extension with the sequence MHHHHHHNVD (SEQ ID NO:30), the entire open reading frame encoded by the Elongin B cDNA was subcloned into the M13mpET-6H bacteriophage vector, (Tan, et al., *BioTechniques* 16: 824–828 (1994)). A 100 ml culture of *E. coli* strain JM109(DE3) was grown to an OD$_{600}$ of 0.6 in SOB medium containing 2.5 mM MgCl$_2$ at 37° C. with gentle shaking. Bacteria were infected at a multiplicity of infection of 10–20. After an additional 2 hours at 37° C., cells were induced with 0.4 mM isopropyl β-D-thiogalactoside, and the culture was incubated an additional 2.5 hours. Bacteria were harvested by centrifugation at 2000×g for 10 min at 4° C., and inclusion bodies were prepared as described, (Lin, K. and Cheng, S. *BioTechniques* 11: 748–753 (1991)), except that RNAase and DNAase treatments were omitted. Inclusion bodies were solubilized by resuspension in 2 ml ice-cold buffer containing 6M guanidine hydrochloride, 40 mM Tris-HCl (pH 7.9), 10 mM imidazole (pH 7.9), 0.5 mM PMSF, and 1 mM DTT. The resulting suspension was clarified by centrifugation at 50,000×g for 20 min at 4° C. and applied to a column containing 1 ml ProBond™ Metal-Binding Resin (Invitrogen) equilibrated with the same buffer. The column was washed with 10 ml of buffer containing 5.8M guanidine hydrochloride, 40 mM Tris-HCl (pH7.9), 40 mM imidazole (pH 7.9), 0.5 mM PMSF, and 1 mM DTT. Histidine-tagged Elongin B was then eluted with 3 ml of buffer containing 4M guanidine hydrochloride, 40 mM Tris (pH 7.9), 300 mM imidazole (pH 7.9), 0.5 mM PMSF, and 1 mM DTT.

Expression of Histidine-tagged Elongin A in *E. coli*

Overexpression of histidine-tagged Elongin A was accomplished using an M13mpET bacteriophage expression system (Tan, et al., *BioTechniques* 16: 824–828 (1994)). To make the expression vector m13mpET-6Hp110, which encodes Elongin A with an 10 amino acid extension with the sequence MHHHHHHNVD (SEQ ID NO:31), the entire open reading frame encoded by the Elongin A cDNA was subcloned into the M13mpET-6H bacteriophage vector. A 100 ml culture of *E. coli* strain JM 109(DE3) was grown to an OD$_{600}$ of 0.6 in SOB medium containing 2.5 mM MgCl$_2$ at 37° C. with gentle shaking. Bacteria were infected at a multiplicity of infection of 10–20. After an additional 2 hours at 37° C., cells were induced with 0.4 mM isopropyl β-D-thiogalactoside, and the culture was incubated an additional 2.5 hours. Bacteria were harvested by centrifugation at 2000×g for 10 min at 4° C., and inclusion bodies were prepared as described (Lin, K. and Cheng, S. *BioTechniques* 11: 748–753 (1991)) except that the RNAase and DNAase treatments were omitted. Inclusion bodies were solubilized by resuspension in 2 ml ice-cold buffer containing 6M guanidine hydrochloride, 40 mM Tris-HCl (pH 7.9), 10 mM imidazole (pH 7.9), 0.5 mM PMSF, and 1 mM DTT. The resulting suspension was clarified by centrifugation at 50,000×g for 20 min at 4° C. and applied to a column containing 1 ml ProBond™ Metal-Binding Resin (Invitrogen) equilibrated with buffer. Thbuffer. The column was washed with 10 ml of buffer containing 5.8M guanidine hydrochloride, 40 mM Tris-HCl (pH 7.9), 40 mM imidazole (pH 7.9), 0.5 mM PMSF, and 1 mM DTT. Histidine-tagged Elongin A was then eluted with 3 ml of buffer containing 4M guanidine hydrochloride, 40 mM Tris (pH 7.9), 300 mM imidazole (pH 7.9), 0.5 mM PMSF, and 1 mM DTT.

EXAMPLE 4

Transcription Activity of Recombinant Elongin

Figure 3:
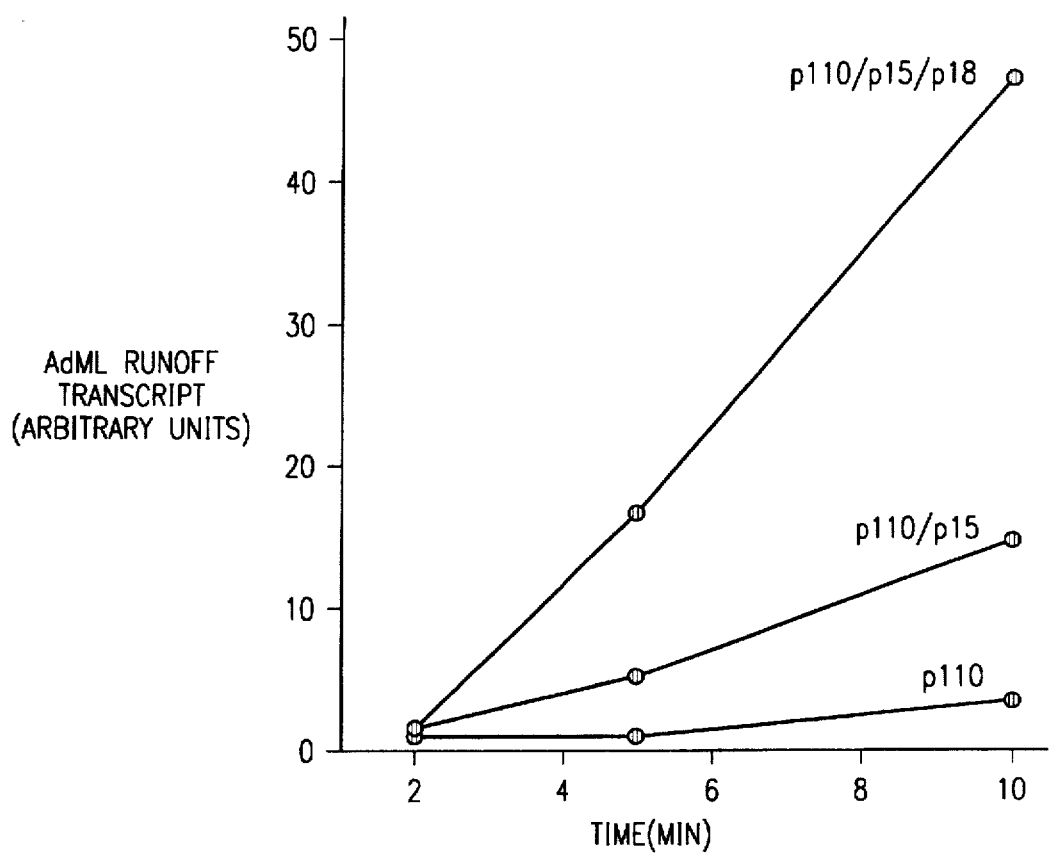
FIG. 3 is a graph depicting the transcriptional activity of recombinantly produced Elongin. In some instances certain subunits were omitted.

To reconstitute Elongin, ~100 ng of recombinant histidine-tagged Elongin B and ~500 ng of recombinant histidine-tagged Elongin A, both in a solution of 4M guanidine hydrochloride, 40 mM Tris-HCl (pH7.9), 300 mM imidazole (pH 7.9), 0.5 mM PMSF, and 1 mM DTT, were added to ~100 ng of lyophilized recombinant Elongin C, which had been prepared as described, (Garrett, et al., *Proc Natl Acad Sci USA* 91: 5237–5241 (1994)). This mixture was diluted ~15 fold with a buffer containing 40 mM HEPES-NaOH (pH 7.9), 100 mM KCl, 2 mM DTT, 50 µM ZnSO$_4$, 0.1 mM EDTA, and 10% (v/v) glycerol and incubated 90 min on ice. Renatured proteins were dialyzed for 2 hours against the same buffer lacking EDTA and DTT. In some experiments, Elongin A, B, or C were omitted from the reconstitution mixture (See FIG. 3). Renatured proteins were assayed for Elongin transcriptional activity as described (Bradsher, et al., *J Biol Chem* 268: 25594–25603 (1993b)); Garrett, et al., *Proc Natl Acad Sci USA* 91: 5237–5241 (1994)).

Maximal stimulation of the rate of accumulation of full length runoff transcripts is dependent on the presence of Elongin A, B, and C. A small stimulation of transcription is observed with Elongin A alone, but neither Elongin B or C nor a combination of Elongin C and Elongin B detectably stimulated transcription. Thus, Elongin C and Elongin B function as positive regulators of Elongin A activity.

EXAMPLE 5

Isolation of cDNA Clones Encoding Human Elongin

Isolation of a CDNA clone encoding human Elongin C

A λZAPII library constructed with cDNA derived from peripheral blood lymphocytes (obtained from Drs. J. Culpeper and F. Lee, DNAX Research Institute, Inc., Palo Alto, Calif.) was screened with an internally labelled, single stranded probe containing rat Elongin C cDNA sequences. The probe was prepared by asymmetric PCR using as template a DNA fragment containing the entire rat Elongin C cDNA. Asymmetric PCR reactions were performed for 30 cycles of 1 min at 94° C., 1 min at 47° C., and 1 min at 72° C. with 1.5 mM MgCl2, 50 µM DATP, 50 µM dGTP, 50 µM dTTP, 100 µCi [α-$^{32}$P] dCTP (3000 Ci/mmole) and an anti-sense oligonucleotide primer, GCA GCG GAT CCT CAA CAA TCT AGG AAG TTC G (SEQ ID NO:32), which contains sequences derived from the 3' end of the rat Elongin C cDNA. Hybridization was at 50° C. for 20 hrs in 5× standard saline citrate (SSC)/5×Denhardt's solution/0.1% SDS/10% dextran sulfate/100 mM NaHPO$_4$/1 ml/ml bovine serum albumin/100 µg/ml herring sperm DNA. Bluescript SK(-) phagemids containing cDNA inserts were rescued with VCS-M13 interference-resistant helper phage (Stratagene) and sequenced by the dideoxy chain-termination method using a Sequenase kit (United States Biochemical Corp.).

The human Elongin C nucleotide sequence is given in SEQ ID NO:7 and the amino acid sequence is listed in SEQ ID NO:8. The human Elongin C cDNA encodes a protein with a predicted amino acid sequence identical to that of rat Elongin C.

These findings indicate that the human Elongin C mRNA is expressed in peripheral blood lymphocytes.

Isolation of a CDNA clone encoding human Elongin B

Oligonucleotide I: GCA ACG TCG ACA TGG ACG TGT TTC TCA TGA T (SEQ ID NO:33), and II: GCA GCG GAT CCT CAC TGC ACA GCT TGT TCA T (SEQ ID NO:34) containing DNA sequences encoding the rat Elongin B amino terminus and carboxyl terminus, respectively, were used in PCR reactions to isolate a human Elongin B cDNA from a λZAPII human peripheral blood lymphocyte cDNA library, which was obtained from J. Culpepper and F. Lee (DNAX Research Institute, Palo Alto, Calif.). PCR reactions were performed for 30 cycles of 1 min at 94° C., 1 min at 46° C., and 2 min at 72° C. with 1.5 mM $MgCl_2$, 0.25 mM dATP, 0.25 mM dCTP, 0.25 mM dGTP, 0.25 mM dTTP, 2.5 units of Taq polymerase, 0.02 A260 units of each primer and ~$4 \times 10^6$ pfu of the library.

PCR products containing Elongin B inserts were identified by Southern blot hybridization using as probe 5'-$\alpha$-$^{32}$P labelled oligonucleotide III, which encodes residues 81-87 of the rat Elongin B subunit. Appropriately sized PCR products were purified by polyacrylamide gel electrophoresis, and subcloned by blunt-end ligation into pBluescript KS(−). Bacteria harboring a recombinant plasmid carrying the human Elongin B cDNA were identified by colony hybridization using oligonucleotide III: GCN GA(C/T) GA(C/T) ACN TT(C/T) GA(G/A) GC (SEQ ID NO:35) as probe.

The resulting cloned PCR product was sequenced by the dideoxy chain termination method using a Sequenase kit. The human Elongin B cDNA encodes a protein with a amino acid sequence that is almost identical to that of rat Elongin B. The human Elongin B nucleotide sequence is given in SEQ ID NO:9 and the corresponding amino acid sequence is listed in SEQ ID NO:10.

These findings indicate that the human Elongin B mRNA is expressed in peripheral blood lymphocytes.

Isolation of a cDNA encoding the human Elongin A cDNAs encoding Elongin A were obtained by screening $1 \times 10^5$ colonies of a pSPORT-1 human umbilical vein endothelial cell (HUVEC) cDNA library with a $^{32}$P-labelled probe comprised of the entire rat Elongin A coding sequence. The library was a gift of Kenji Fukudome (Oklahoma Medical Research Foundation). Prehybridization was carried out for 2 hrs at 42° C. in 4×SSC, 0.1% SDS, 40% formamide, 20 mM Tris-HCl (pH 7.5), 4% dextran sulfate, 1×Denhardt's solution, 100 µg/ml salmon sperm DNA. Hybridization was carried out for 16 hr at 42° C. in the above buffer containing radiolabelled probe. Colony lifts were washed twice for 15 min at 42° C. in 2×SSC containing 0.1% SDS. Positive bacterial colonies were purified by two additional rounds of screening under the same conditions except that hybridization was carried out at 45° C., and the two washes were performed at 45° C. for 20 min each. A positive clone (HUVEC-p110-8) containing the largest insert was sequenced and found to contain all but the 5' end of the human Elongin A.

To obtain the 5' end of the human Elongin A cDNA, an aliquot of human liver 5'-RACEReady cDNA (obtained from CLONTECH) was used as a template in PCR reactions. The primary PCR reaction was carried out with the Anchor primer provided by the manufacturer and a primer designated ELA1 (5'-GCTTTCTCCCTTGCATTGTCCC-3') (SEQ ID NO:36), which contains a sequence located near the 5' end of the HUVEC-p110-8 cDNA. A small dilution of the primary PCR reaction products was then used in a secondary PCR reaction with the Anchor primer and the nested primer ELA2 (5'-CCTCTAGAATTTCTCTCTGCTCACCACAGG-3') (SEQ ID NO:37), which contains a sequence located closer to the 5' end of the HUVEC-p110-8 CDNA than ELA1. The product of the second PCR reaction was gel-purified and subcloned into pUC-18. The clone with the largest insert (Liver-p110-4) was sequenced. Liver-p110-4 precisely overlapped the 5' end of HUVEC-p110-8 and extended further 5' by 818 bp. The predicted open reading frame of the human Elongin A cDNA encodes a 772 amino acid protein, which is 840 identical to rat p110.

EXAMPLE 6

Expression of human Elongin A in *E. coli* and assay of recombinant human Elongin A transcriptional activity The expression vector pET 16b-hp110 was constructed by inserting a PCR generated fragment containing the complete human Elongin A open reading frame into the Nde I and Bam HI sites of pET16b (Novagen). *E. coli* strain BL21 (DE3) transformed with pET16b-hp110 was grown in LB medium containing 50 14g/ml ampicillin at 370 C. The culture was induced by addition of 1 mM 1PTG when it reached an optical density at 600 mM ($OD_{600}$) of 0.6. After 2.5 hr, cells were harvested by centrifugation at 2000×g for 10 min at 4° C. Inclusion bodies were prepared essentially as described (Lin, K. and Cheng, S. (1991) BioTechniques 11, 748–753), except that DNAase and RNAase treatments were omitted. Inclusion bodies were solubilized by resuspension in 5 ml of ice cold 50 mM Tris-HCl (pH 8.0) containing 6M guanidine hydrocholoride. The resulting suspension was clarified by centrifugation at 50,000×g for 20 min at 4° C. Histidine-tagged human Elongin A was purified from the supernatant by affinity chromatography on Pro-Bond metal binding resin (Invitrogen) according to the manufacturer's instructions.

The ability of recombinant human Elongin A to support SIII transcription activity when renatured with recombinant Elongin C and Elongin B was tested by the same procedures used to analyze the transcription activity of recombinant rat Elongin A. Recombinant human Elongin A is transcriptionally active.

Although Elongin A contains no structural motifs characteristic of transcription factors, such as zinc finger, leucine zipper, or helix-turn-helix domains, a homology search of the GenBank data base revealed that the N-terminus of Elongin A shares significant sequence similarity with the N-terminus of RNA polymerase II elongation factor SII. The two proteins are 29% identical over a 108-amino acid overlap; when conservative amino acid substitutions are included, the sequence similarity is 53%, suggesting that SII and Elongin A are members of a family of related transcription factors. SII N-terminal sequences similar to Elongin A include a phosphorylation domain proposed to regulate SII activity in vivo; this SII region, however, is dispensable for SII transcriptional activity in vitro.

By analyzing a series of N- and C-terminal Elongin A deletion mutants, we observed that Elongin A transcriptional activity resides in a 280 amino acid region that includes residues between 400 and 680. Interestingly, within this essential region (between amino acids 530 and 548) is a near-consensus eukaryotic DNA topoisomerase I active site which includes a tyrosine residue at position 543 in rat and position 544 in human Elongin A. The tyrosine residue within this motif is expected to be critical for topoisomerase activity; however, mutation of this residue has no effect on Elongin A transcriptional activity in vitro.

EXAMPLE 7

Elongin Effect on Transcription Rate

Materials

Unlabelled ultrapure ribonucleoside 5'-triphosphates and dATP were from Pharmacia LKB Biotechnology, Inc. AMP-PNP was obtained from Sigma or Pharmacia. [$\alpha$-$^{32}$P] CTP (>650 Ci/mmol) and [$\alpha$-$^{32}$P] UTP (>650 Ci/mmol) were obtained from ICN. Sarkosyl and heparin were from Sigma. Bovine serum albumin (Pentex fraction V) was obtained from ICN Immunobiologicals. Agarose (GenAR) was from Mallinckrodt (St. Louis, Mo.).

Preparation of RNA polymerase II and transcription factors

Elongin was purified from rat liver nuclear extracts as described in Example 1. Recombinant yeast TFIID was expressed and purified as described (Conaway, et al., *J Biol Chem* 266: 7804–7811 (1991)) from bacterial strain N5151 containing the plasmid pASY2FD (Schmidt, et al., *Proc Natl Acad Sci USA* 86: 7785–7789 (1989)). Recombinant rat TFIID was expressed in *Escherichia coli* using T7-expression vector pET-11a (Novagen) and was purified from extracts by chromatography on DEAE Sepharose and heparin Sepharose as described (Hoey, et al., *Cell* 61: 1179–1186 (1990)). Recombinant rat α(TFIIB) (Tsuboi, et al., *Nucleic Acids Res* 20: 3250 (1992)) and recombinant human TFIIE (Peterson, et al., *Nature* 354: 369–373 (1991)) were prepared as described, except that the 56 kDa subunit of TFIIE was expressed in BL21(DE3). Recombinant βγ(TFIIF) was purified by phosphocellulose chromatography (Conaway, J. W. and Conaway, R. C., *J Biol Chem* 264: 2357–2362 (1989)), of whole cell extracts prepared from Sf21 cells co-infected with recombinant baculoviruses encoding human RAP74 (Aso, et al., *Nature* 355: 461–464 (1992); Finkelstein, et al., *Nature* 355: 464–467 (1992)) and rat RAP30 (Garrett, et al., *J Biol Chem* 267: 23942–23949 (1992)). Recombinant viruses were constructed using the BacPAK6 baculovirus expression system (Clontech). RNA polymerase II (Serizawa, et al., *Proc Natl Acad Sci USA* 89: 7476–7480 (1992)), the native rat TATA factor τ (Conaway, et al., *J Biol Chem* 265: 7552–7558 (1990)), and transcription factor δ (BTF2) (Conaway, R. C. and Conaway, J. W., *Proc Natl Acad Sci USA* 86: 7356–7360 (1989)); Conaway, et al., *J Biol Chem* 267: 10142–10148) (1992)) were purified from rat liver as previously described.

Assay of runoff transcription

Unless indicated otherwise, preinitiation complexes were assembled as described (Conaway, et al., *J Biol Chem* 262: 8293–8297 (1987)) by preincubation of 100 ng of Nde I-digested pDN-AdML (Conaway, R. C. and Conaway, J. W., *J Biol Chem* 263: 2962–2968 (1988)), 100 ng of Nde I-digested pN$_4$ (Lorch, et al., *Cell* 49: 203–210 (1987)), or 10 ng of the Eco RI to Nde I fragment from pDN-AdML, and approximately 10 ng of recombinant α (TFIIB), 10 ng of recombinant βγ (TFIIF), 7 ng of recombinant human TFIIE, 40 ng of δ (BTF2) (Fraction VI), 60 ng T (Fraction V) or 50 ng of recombinant yeast TFIID (AcA 44 fraction), and 0.01 unit of RNA polymerase II. Transcription was initiated by addition of 7 mM MgCl$_2$ and ribonucleoside triphosphates in the concentrations noted below. After incubation at 28° C., runoff transcripts were analyzed by electrophoresis through 6% polyacrylamide/7.0M urea gels. Transcription was quantitated by densitometry of autoradiograms using an LKB UltroScan XL laser densitometer.

Isolation of DNA fragments

DNA fragments were excised from 1.5% agarose gels and purified using GENECLEAN II (BIO 101 Inc.) according to the manufacturer's instructions.

Determination of Transcription Rate

AMP-PNP is used less well than ATP as a substrate for RNA chain elongation (Ernst, et al., *Mol Cell Biol* 3: 2172–2179 (1983)). At AMP-PNP concentrations <10 μM, full length runoff transcripts initiated from the AdML promoter do not accumulate, but there is a substantial accumulation of shorter products. At AMP-PNP concentrations >10 μM, significant synthesis of full length runoff transcripts is observed. Furthermore, the short RNA products formed in the presence of low concentrations of AMP-PNP can be chased into full length runoff transcripts if ATP is added to reaction mixtures after the addition of heparin, which inhibits promoter-specific transcription initiation but not elongation of previously initiated RNA chains (Conaway, R. C. and Conaway, J. W., *J Biol Chem* 265: 7559–7563 (1990); Egly, et al., *EMBO J* 3: 2363–2371 (1984)). Regardless of the AMP-PNP concentration present in reaction mixtures prior to the ATP chase, roughly equivalent levels of runoff transcripts were synthesized from the AdML promoter following addition of heparin and ATP. Thus, the short transcripts formed in the presence of low AMP-PNP concentrations and in the absence of Elongin are not terminated, but, rather, appear to be contained in transcriptionally active but stalled RNA polymerase II elongation complexes.

To determine whether the effect of Elongin is a general or whether it is specific for reactions in which AMP-PNP replaces ATP as a substrate for RNA chain elongation, runoff transcription assays were performed, with and without Elongin, in which the concentration of each of the four ribonucleoside triphosphates was lowered individually in the presence of fixed concentrations of the other three ribonucleoside triphosphates. Elongin is able to stimulate synthesis of accurately initiated transcripts when reactions are carried out with limiting concentrations of any of the ribonucleoside triphosphates. During a 30 min incubation, maximal stimulation of transcription was observed when the limiting ribonucleoside triphosphate was included in reaction mixtures at concentrations less than 2 μM. The extent to which Elongin stimulates accumulation of full length products appears to differ depending on which ribonucleoside triphosphate is limiting.

Figure 2:
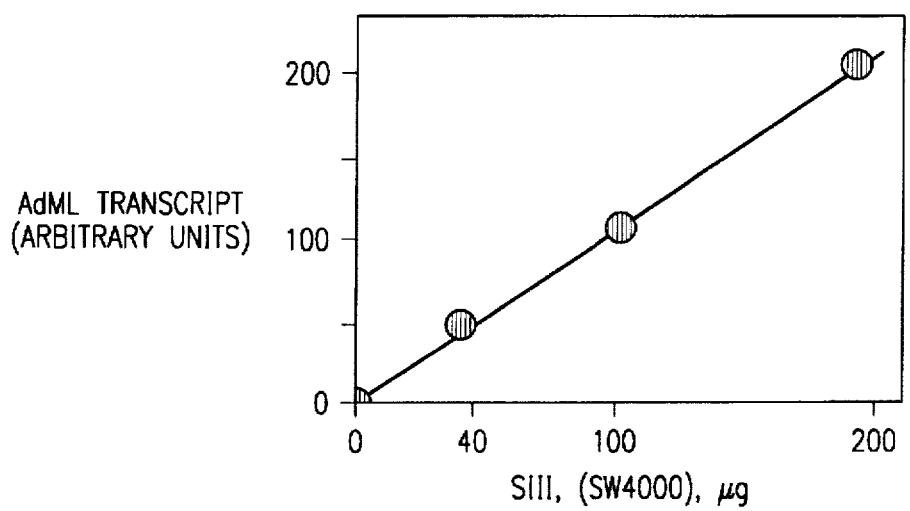
FIG. 2 is a graph depicting the results of runoff transcription assays which illustrate Elongin stimulation of transcription in a dose-dependent manner.

Examination of the kinetics of accumulation of full-length runoff transcripts revealed that Elongin significantly increases the rate of incorporation of ribonucleoside triphosphates into growing RNA chains. (See FIG. 2) An investigation of the effect of Elongin on runoff transcription was also carried out in the presence of limiting UTP. Under these conditions, full-length runoff transcripts synthesized in the absence of Elongin were first detected approximately 24 min after addition of ribonucleoside triphosphates. In contrast, full-length runoff transcripts synthesized in the presence of Elongin were detected within 4 min after addition of ribonucleoside triphosphates.

Transcriptional stimulation by Elongin is not limited to cases in which one or more of the ribonucleoside triphosphates are present in reaction mixtures at very low concentrations. Analysis of the effect of Elongin on transcription at very early times after initiation indicates that the factor also increases the rate of accumulation of full-length runoff transcripts synthesized in the presence of ribonucleoside triphosphates at the concentrations (50 μM ATP, 50 μM UTP, 50 μM GTP, and 10 μM CTP) normally used in our standard transcription assays. Under these conditions, full-length runoff transcripts synthesized in the absence of Elongin were first detected ~6 min after addition of ribonucleoside triphosphates. In contrast, full-length runoff transcripts synthesized in the presence of Elongin could be detected within 1 min after addition of ribonucleoside triphosphates. Thus, Elongin stimulates the rate of RNA chain elongation at least five-fold when transcription is carried out both at very low ribonucleoside triphosphate concentrations and at ribonucleoside triphosphate concentrations used in our standard runoff transcription assays. In addition, we observed that Elongin is able to stimulate the rate of RNA chain elongation to a similar extent when all nucleotides are at a concentration of 500 μM.

Although there is synthesis of multiple short transcripts when transcription is carried out in the presence of limiting AMP-PNP or UTP, most of these transcripts can be chased into full-length runoff transcripts either by increasing the concentration of the limiting nucleotide or by addition of Elongin indicating that RNA polymerase II pauses at multiple sites during synthesis of transcripts initiated from the AdML promoter on pDN-AdML, (Conaway, R. C. and Conaway, J. W., *J Biol Chem* 263: 2962-2968 (1988)). To determine whether RNA polymerase II pauses at these sites simply as a consequence of limiting levels of ribonucleoside triphosphates or whether polymerase pauses in response to specific DNA sequences that promote pausing regardless of ribonucleoside triphosphate concentration, we compared the lengths of short transcripts synthesized in the presence of low concentrations of each of the four ribonucleoside triphosphates. Distinct sets of RNA products are synthesized in the presence of low concentrations of UTP, ATP, GTP, and CTP, suggesting that most of the RNA polymerase II elongation complexes are not pausing at DNA-sequences that function as specific pause signals. Instead, pause sites appear to be specific for and induced by the limiting ribonucleoside triphosphate. It is noteworthy that, although the 3' termini of RNA in paused elongation complexes have not been established unequivocally, most of them map roughly to DNA sequences encoding two or more sequential residues of the limiting nucleotide (data not shown).

Like Elongin, the general initiation factor βγ(TFIIF) has been shown previously to stimulate the rate of RNA chain elongation by RNA polymerase II (Price, et al., *Mol Cell Biol* 9: 1465-1475 (1989); Flores, et al., *J Biol Chem* 264: 8913-8921 (1989); Bengal, et al., *Mol Cell Biol* 11: 1195-1206 (1991); Kato, et al., *Genes Dev* 6: 655-666 (1992); and Izban, M. G. and Luse, D. S., *J Biol Chem* 267: 13647-13655 (1992)). The ability of the two factors to stimulate transcription initiated at the oligo-dC tail of pCpGR220 S/P/X or at the AdML promoter was compared. The recombinant βγ(TFIIF) used in these experiments was expressed in and purified from insect cells and was more than 95% pure.

In another procedure, transcription was initiated by addition of purified RNA polymerase II to reaction mixtures containing pCpGR220 S/P/X and 50 μM ATP, 50 μM GTP, and 2 μM [$\alpha^{32}$-P] CTP. After a 30 min incubation to allow synthesis of short, labelled transcripts, the accumulated transcripts were chased with 500 μM non-radioactive CTP, ATP, GTP, and UTP, in the presence or absence of Elongin or γγ(TFIIF). Under these conditions, both βγ(TFIIF) and Elongin strongly stimulate the rate of RNA chain elongation. We estimate that transcription elongation in the presence of either factor is approximately 500 nucleotides/minute.

Preinitiation complexes were assembled at the AdML promoter by preincubation of template DNA with RNA polymerase II and initiation factors; reactions contained an amount of αγ(TFIIF) just sufficient to produce maximal levels of initiation. Transcription was then initiated by addition of ATP, GTP, and a low concentration of UTP and [($\alpha$-$^{32}$-P] CTP. After a 12 min incubation to allow synthesis of short labelled transcripts, the radioactive CTP was diluted by addition of an approximately 30-fold excess of non-radioactive CTP, and varying amounts of Elongin or additional αγ(TFIIF) were added to reactions. Under some of these conditions, Elongin strongly stimulates accumulation of full length runoff transcripts from the AdML promoter. Likewise, addition of βγ(TFIIF), in quantities greater than that sufficient to saturate the reaction for initiation, stimulates accumulation of full length runoff transcripts.

We claim:

1. A purified transcription factor which is a heterotrimeric protein consisting of a single copy each of:

(a) a first protein subunit comprising the amino acid sequence set forth as SEQ ID NO:2;

(b) a second protein subunit comprising the amino acid sequence set forth as SEQ ID NO:4; and (c) a third protein subunit comprising the amino acid sequence set forth as SEQ ID NO:6.

2. A purified polypeptide comprising the amino acid sequence set forth as SEQ ID NO:2.

3. A purified polypeptide comprising the amino acid sequence set forth as SEQ ID NO:4.

4. A purified polypeptide comprising the amino acid sequence set forth as SEQ ID NO:6.

5. A purified transcription factor which is a heterotrimeric protein consisting of a single copy each of:

(a) a first protein subunit comprising the amino acid sequence set forth as SEQ ID NO:8;

(b) a second protein subunit comprising the amino acid sequence set forth as SEQ ID NO:10; and (c) a third protein subunit comprising the amino acid sequence set forth as SEQ ID NO:12.

6. A purified polypeptide comprising the amino acid sequence set forth as SEQ ID NO:8.

7. A purified polypeptide comprising the amino acid sequence set forth as SEQ ID NO:10.

8. A purified polypeptide comprising the amino acid sequence set forth as SEQ ID NO:12.

* * * * *

UNITED STATES PATENT AND TRADEMARK OFFICE
CERTIFICATE OF CORRECTION

PATENT NO. : 5,792,634
DATED : August 11, 1998
INVENTOR(S) : Ronald C. Conaway, et al.

It is certified that error appears in the above-identified patent and that said Letters Patent is hereby corrected as shown below:

Column 2,
Line 15, change "PAP" to "RAP".
Line 23, change "*Saccharomnyces*" to "*Saccharomyces*".

Column 3,
Line 30, change "eukarotic" to "eukaryotic".

Column 5,
Line 10, change "nt/mmn" to "nt/min".
Line 59, after "40%", delete "is".

Column 13,
Line 43, change "XZAP" to "λZAP".

Column 14,
Line 18, change "(SSC)/1+" to (SSC)1X".

Column 15,
Line 53, change "buffer. Thbuffer" to " the same buffer".

Column 17,
Line 35, change "HCI" to HC1".
Line 67, chagne "840" to "84%".

Column 18,
Line 9, "14g/ml" to "µg/ml".
Line 9, change "370" to "37°"
Line 11, change "mM" to "nm".

Column 19,
Line 43, change "60 ng T" to "60 ng τ".

UNITED STATES PATENT AND TRADEMARK OFFICE
CERTIFICATE OF CORRECTION

PATENT NO. : 5,792,634
DATED : August 11, 1998
INVENTOR(S) : Ronald C. Conaway, et al.

It is certified that error appears in the above-identified patent and that said Letters Patent is hereby corrected as shown below:

Column 22,
Line 13, change "γγ(TFIIF) to "βγ(TFIIF)"
Line 20, change "αγ(TFIIF) to "βγ(TFIIF)"
Line 27, change "αγ(TFIIF) to "βγ(TFIIF)"

Signed and Sealed this

Twenty-seventh Day of November, 2001

Attest:

NICHOLAS P. GODICI
Attesting Officer
Acting Director of the United States Patent and Trademark Office

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
( A ) LENGTH: 458 base pairs
( B ) TYPE: nucleic acid
( C ) STRANDEDNESS: both
( D ) TOPOLOGY: both ( i i ) MOLECULE TYPE: cDNA ( i x ) FEATURE:
( A ) NAME/KEY: CDS
( B ) LOCATION: 46..381

( x i ) SEQUENCE DESCRIPTION: SEQ ID NO:1:

```
ACTAGTAACT  TCCTCTGGGA  TCAAATAGAA  TTTTATAAGA  ACACA ATG GAT GGA                    54
                                                      Met Asp Gly
                                                        1

GAG GAG AAA ACC TAT GGT GGC TGT GAA GGC CCT GAT GCC ATG TAT GTG              102
Glu Glu Lys Thr Tyr Gly Gly Cys Glu Gly Pro Asp Ala Met Tyr Val
      5                   10                  15

AAA TTA ATA TCT TCT GAT GGT CAT GAA TTT ATT GTA AAA AGA GAA CAT             150
Lys Leu Ile Ser Ser Asp Gly His Glu Phe Ile Val Lys Arg Glu His
 20                  25                  30                  35

GCA TTA ACA TCA GGA ACA ATA AAG GCC ATG TTG AGT GGT CCA GGT CAG             198
Ala Leu Thr Ser Gly Thr Ile Lys Ala Met Leu Ser Gly Pro Gly Gln
                 40                  45                  50
```

| | | | | | | | | | | | | | | | | |
|---|---|---|---|---|---|---|---|---|---|---|---|---|---|---|---|---|
| TTT | GCG | GAG | AAT | GAA | ACC | AAT | GAG | GTC | AAC | TTT | AGA | GAG | ATC | CCT | TCA | 246 |
| Phe | Ala | Glu | Asn | Glu | Thr | Asn | Glu | Val | Asn | Phe | Arg | Glu | Ile | Pro | Ser | |
| | | | 55 | | | | 60 | | | | | | 65 | | | |
| CAT | GTG | CTA | TCG | AAA | GTG | TGC | ATG | TAT | TTT | ACC | TAC | AAG | GTC | CGC | TAT | 294 |
| His | Val | Leu | Ser | Lys | Val | Cys | Met | Tyr | Phe | Thr | Tyr | Lys | Val | Arg | Tyr | |
| | | 70 | | | | | 75 | | | | | 80 | | | | |
| ACT | AAC | AGC | TCC | ACT | GAA | ATT | CCT | GAA | TTC | CCA | ATT | GCA | CCT | GAA | ATT | 342 |
| Thr | Asn | Ser | Ser | Thr | Glu | Ile | Pro | Glu | Phe | Pro | Ile | Ala | Pro | Glu | Ile | |
| | 85 | | | | | | 90 | | | | | 95 | | | | |
| GCA | CTG | GAA | CTG | CTG | ATG | GCC | GCG | AAC | TTC | CTA | GAT | TGT | TAAATAAAT | | | 391 |
| Ala | Leu | Glu | Leu | Leu | Met | Ala | Ala | Asn | Phe | Leu | Asp | Cys | | | | |
| 100 | | | | | 105 | | | | | 110 | | | | | | |

AAATTATAAT AAACTGTTAA AAAAAAAAAA AAAAAAAAAA AAAAAAAAAA AAAAAAAAAA 451

AAAAAAA 458

(2) INFORMATION FOR SEQ ID NO:2:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met | Asp | Gly | Glu | Glu | Lys | Thr | Tyr | Gly | Gly | Cys | Glu | Gly | Pro | Asp | Ala |
| 1 | | | | 5 | | | | | 10 | | | | | 15 | |
| Met | Tyr | Val | Lys | Leu | Ile | Ser | Ser | Asp | Gly | His | Glu | Phe | Ile | Val | Lys |
| | | | 20 | | | | | 25 | | | | | 30 | | |
| Arg | Glu | His | Ala | Leu | Thr | Ser | Gly | Thr | Ile | Lys | Ala | Met | Leu | Ser | Gly |
| | | | 35 | | | | | 40 | | | | | 45 | | |
| Pro | Gly | Gln | Phe | Ala | Glu | Asn | Glu | Thr | Asn | Glu | Val | Asn | Phe | Arg | Glu |
| | | 50 | | | | | 55 | | | | | 60 | | | |
| Ile | Pro | Ser | His | Val | Leu | Ser | Lys | Val | Cys | Met | Tyr | Phe | Thr | Tyr | Lys |
| 65 | | | | | 70 | | | | | 75 | | | | | 80 |
| Val | Arg | Tyr | Thr | Asn | Ser | Ser | Thr | Glu | Ile | Pro | Glu | Phe | Pro | Ile | Ala |
| | | | | 85 | | | | | 90 | | | | | 95 | |
| Pro | Glu | Ile | Ala | Leu | Glu | Leu | Leu | Met | Ala | Ala | Asn | Phe | Leu | Asp | Cys |
| | | | 100 | | | | | 105 | | | | | 110 | | |

(2) INFORMATION FOR SEQ ID NO:3:

(i) SEQUENCE CHARACTERISTICS:
        (A) LENGTH: 354 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..354

(xi) SEQUENCE DESCRIPTION: SEQ ID NO:3:

| | | | | | | | | | | | | | | | | |
|---|---|---|---|---|---|---|---|---|---|---|---|---|---|---|---|---|
| ATG | GAC | GTG | TTT | CTC | ATG | ATC | CGG | CGC | CAC | AAG | ACC | ACC | ATC | TTT | ACG | 48 |
| Met | Asp | Val | Phe | Leu | Met | Ile | Arg | Arg | His | Lys | Thr | Thr | Ile | Phe | Thr | |
| 1 | | | | 5 | | | | | 10 | | | | | 15 | | |
| GAC | GCC | AAG | GAG | TCG | AGC | ACG | GTG | TTC | GAA | CTG | AAG | CGC | ATC | GTC | GAG | 96 |
| Asp | Ala | Lys | Glu | Ser | Ser | Thr | Val | Phe | Glu | Leu | Lys | Arg | Ile | Val | Glu | |
| | | | 20 | | | | | 25 | | | | | 30 | | | |
| GGC | ATC | CTC | AAG | CGG | CCG | CCA | GAG | GAG | CAG | CGG | CTG | TAC | AAG | GAC | GAC | 144 |

|     |     |     |     |     |     |     |     |     |     |     |     |     |     |     |     |
|-----|-----|-----|-----|-----|-----|-----|-----|-----|-----|-----|-----|-----|-----|-----|-----|
| Gly | Ile | Leu | Lys | Arg | Pro | Pro | Glu | Glu | Gln | Arg | Leu | Tyr | Lys | Asp | Asp |
|     |     | 35  |     |     |     |     | 40  |     |     |     |     | 45  |     |     |     |

| CAG | CTC | CTT | GAT | GAT | GGA | AAA | ACT | CTG | GGC | GAA | TGT | GGC | TTC | ACC | AGT | 192 |
|-----|-----|-----|-----|-----|-----|-----|-----|-----|-----|-----|-----|-----|-----|-----|-----|-----|
| Gln | Leu | Leu | Asp | Asp | Gly | Lys | Thr | Leu | Gly | Glu | Cys | Gly | Phe | Thr | Ser |     |
|     | 50  |     |     |     |     | 55  |     |     |     |     | 60  |     |     |     |     |     |

| CAG | ACA | GCA | AGG | CCA | CAG | GCC | CCA | GCC | ACA | GTG | GGC | CTG | GCC | TTT | CGA | 240 |
|-----|-----|-----|-----|-----|-----|-----|-----|-----|-----|-----|-----|-----|-----|-----|-----|-----|
| Gln | Thr | Ala | Arg | Pro | Gln | Ala | Pro | Ala | Thr | Val | Gly | Leu | Ala | Phe | Arg |     |
| 65  |     |     |     |     | 70  |     |     |     |     | 75  |     |     |     |     | 80  |     |

| GCA | GAT | GAC | ACC | TTT | GAA | GCG | CTG | CGT | ATT | GAA | CCC | TTC | TCC | AGC | CCT | 288 |
|-----|-----|-----|-----|-----|-----|-----|-----|-----|-----|-----|-----|-----|-----|-----|-----|-----|
| Ala | Asp | Asp | Thr | Phe | Glu | Ala | Leu | Arg | Ile | Glu | Pro | Phe | Ser | Ser | Pro |     |
|     |     |     |     | 85  |     |     |     |     | 90  |     |     |     |     | 95  |     |     |

| CCG | GAG | CTT | CCA | GAT | GTG | ATG | AAG | CCA | CAG | GAT | TCT | GGA | GGC | AGT | GCC | 336 |
|-----|-----|-----|-----|-----|-----|-----|-----|-----|-----|-----|-----|-----|-----|-----|-----|-----|
| Pro | Glu | Leu | Pro | Asp | Val | Met | Lys | Pro | Gln | Asp | Ser | Gly | Gly | Ser | Ala |     |
|     |     |     | 100 |     |     |     |     | 105 |     |     |     |     | 110 |     |     |     |

| AAT | GAA | CAA | GCT | GTG | CAG |     |     |     |     |     |     |     |     |     |     | 354 |
|-----|-----|-----|-----|-----|-----|-----|-----|-----|-----|-----|-----|-----|-----|-----|-----|-----|
| Asn | Glu | Gln | Ala | Val | Gln |     |     |     |     |     |     |     |     |     |     |     |
|     |     | 115 |     |     |     |     |     |     |     |     |     |     |     |     |     |     |

( 2 ) INFORMATION FOR SEQ ID NO:4:

( i ) SEQUENCE CHARACTERISTICS:
        ( A ) LENGTH: 118 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Asp | Val | Phe | Leu | Met | Ile | Arg | Arg | His | Lys | Thr | Thr | Ile | Phe | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Ala | Lys | Glu | Ser | Ser | Thr | Val | Phe | Glu | Leu | Lys | Arg | Ile | Val | Glu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Ile | Leu | Lys | Arg | Pro | Pro | Glu | Glu | Gln | Arg | Leu | Tyr | Lys | Asp | Asp |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Gln | Leu | Leu | Asp | Asp | Gly | Lys | Thr | Leu | Gly | Glu | Cys | Gly | Phe | Thr | Ser |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Gln | Thr | Ala | Arg | Pro | Gln | Ala | Pro | Ala | Thr | Val | Gly | Leu | Ala | Phe | Arg |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ala | Asp | Asp | Thr | Phe | Glu | Ala | Leu | Arg | Ile | Glu | Pro | Phe | Ser | Ser | Pro |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Pro | Glu | Leu | Pro | Asp | Val | Met | Lys | Pro | Gln | Asp | Ser | Gly | Gly | Ser | Ala |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Asn | Glu | Gln | Ala | Val | Gln |
|-----|-----|-----|-----|-----|-----|
|     |     | 115 |     |     |     |

( 2 ) INFORMATION FOR SEQ ID NO:5:

( i ) SEQUENCE CHARACTERISTICS:
        ( A ) LENGTH: 3501 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 82..2403

( i x ) FEATURE:
        ( A ) NAME/KEY: misc_difference
        ( B ) LOCATION: replace(2990, "")
        ( D ) OTHER INFORMATION: /note= "This base can be either a,
            c, t, g."

( x i ) SEQUENCE DESCRIPTION: SEQ ID NO:5:

| | | | | | | | | | | |
|---|---|---|---|---|---|---|---|---|---|---|
| CGTTGCTGTC | GAGGGCGGAG | TTGCGGCCCG | AGGACGCTAC | GCGAGCCCAG | TTCCGGCGAG | | | | | 60 |

| | | | | | | | | | | | | | | | | | |
|---|---|---|---|---|---|---|---|---|---|---|---|---|---|---|---|---|---|
| GAGGCCGCGC | CAGTGACAGC | G | ATG | GCG | GCG | GAG | TCG | GCG | CTC | CAA | GTT | GTG | | | | | 111 |
| | | | Met | Ala | Ala | Glu | Ser | Ala | Leu | Gln | Val | Val | | | | | |
| | | | 1 | | | | 5 | | | | | 10 | | | | | |

| GAG | AAG | CTG | CAG | GCG | CGC | CTG | GCT | GCG | AAC | CCG | GAC | CCC | AAG | AAG | CTA | 159 |
|---|---|---|---|---|---|---|---|---|---|---|---|---|---|---|---|---|
| Glu | Lys | Leu | Gln | Ala | Arg | Leu | Ala | Ala | Asn | Pro | Asp | Pro | Lys | Lys | Leu | |
| | | | | 15 | | | | | 20 | | | | | 25 | | |

| TTG | AAA | TAT | TTG | AAG | AAA | CTT | TCC | GTC | TTA | CCT | ATT | ACA | GTA | GAC | ATT | 207 |
|---|---|---|---|---|---|---|---|---|---|---|---|---|---|---|---|---|
| Leu | Lys | Tyr | Leu | Lys | Lys | Leu | Ser | Val | Leu | Pro | Ile | Thr | Val | Asp | Ile | |
| | | | 30 | | | | | 35 | | | | | 40 | | | |

| CTT | GTG | GAG | ACT | GGG | GTG | GGG | AAA | ACA | GTG | AAC | AGC | TTT | CGG | AAA | CAT | 255 |
|---|---|---|---|---|---|---|---|---|---|---|---|---|---|---|---|---|
| Leu | Val | Glu | Thr | Gly | Val | Gly | Lys | Thr | Val | Asn | Ser | Phe | Arg | Lys | His | |
| | | 45 | | | | | 50 | | | | | 55 | | | | |

| GAG | CAA | GTG | GGA | AAC | TTT | GCC | AGA | GAC | CTG | GTT | GCC | CAG | TGG | AAG | AAG | 303 |
|---|---|---|---|---|---|---|---|---|---|---|---|---|---|---|---|---|
| Glu | Gln | Val | Gly | Asn | Phe | Ala | Arg | Asp | Leu | Val | Ala | Gln | Trp | Lys | Lys | |
| | | 60 | | | | 65 | | | | | 70 | | | | | |

| CTG | GTT | CCA | GTA | GAA | CGA | AAC | AAT | GAG | GCT | GAG | GAT | CAG | GAT | TTT | GAG | 351 |
|---|---|---|---|---|---|---|---|---|---|---|---|---|---|---|---|---|
| Leu | Val | Pro | Val | Glu | Arg | Asn | Asn | Glu | Ala | Glu | Asp | Gln | Asp | Phe | Glu | |
| 75 | | | | | 80 | | | | | 85 | | | | | 90 | |

| AAG | AGC | AAT | TCC | CGC | AAG | CGT | CCC | CGA | GAT | GTT | CCC | CAG | CAG | GAG | GAG | 399 |
|---|---|---|---|---|---|---|---|---|---|---|---|---|---|---|---|---|
| Lys | Ser | Asn | Ser | Arg | Lys | Arg | Pro | Arg | Asp | Val | Pro | Gln | Gln | Glu | Glu | |
| | | | | 95 | | | | | 100 | | | | | 105 | | |

| GAA | GCG | GAG | GGG | AAC | TAC | CAG | GAA | AGC | TGG | CAA | GCC | TCA | GGC | AGC | CAG | 447 |
|---|---|---|---|---|---|---|---|---|---|---|---|---|---|---|---|---|
| Glu | Ala | Glu | Gly | Asn | Tyr | Gln | Glu | Ser | Trp | Gln | Ala | Ser | Gly | Ser | Gln | |
| | | | 110 | | | | | 115 | | | | | 120 | | | |

| CCC | TAC | AGC | CCT | GAG | CAC | AGA | CAG | AAA | AAG | CAC | AGA | AAA | CTT | CCT | GAG | 495 |
|---|---|---|---|---|---|---|---|---|---|---|---|---|---|---|---|---|
| Pro | Tyr | Ser | Pro | Glu | His | Arg | Gln | Lys | Lys | His | Arg | Lys | Leu | Pro | Glu | |
| | | 125 | | | | | 130 | | | | | 135 | | | | |

| CTT | GAA | AGG | CCT | CAC | AAA | GTG | GCT | CAT | GGT | CAC | GAG | AGG | AGA | GAT | GAA | 543 |
|---|---|---|---|---|---|---|---|---|---|---|---|---|---|---|---|---|
| Leu | Glu | Arg | Pro | His | Lys | Val | Ala | His | Gly | His | Glu | Arg | Arg | Asp | Glu | |
| | 140 | | | | | 145 | | | | | 150 | | | | | |

| AGG | AAG | AGG | TGT | CAC | AAA | GTG | TCA | CCA | CCA | TAT | TCT | TCA | GAC | CCC | GAG | 591 |
|---|---|---|---|---|---|---|---|---|---|---|---|---|---|---|---|---|
| Arg | Lys | Arg | Cys | His | Lys | Val | Ser | Pro | Pro | Tyr | Ser | Ser | Asp | Pro | Glu | |
| 155 | | | | | 160 | | | | | 165 | | | | | 170 | |

| TCG | TCT | GAC | TAT | GGT | CAT | GTT | CAA | TCT | CCT | CCA | CCT | TCA | AGT | CCC | CAT | 639 |
|---|---|---|---|---|---|---|---|---|---|---|---|---|---|---|---|---|
| Ser | Ser | Asp | Tyr | Gly | His | Val | Gln | Ser | Pro | Pro | Pro | Ser | Ser | Pro | His | |
| | | | | 175 | | | | | 180 | | | | | 185 | | |

| CAA | ATG | TAT | ACA | GAC | CTC | TCT | AGG | TCC | CCA | GAG | ATG | GAC | CAG | GAA | CCC | 687 |
|---|---|---|---|---|---|---|---|---|---|---|---|---|---|---|---|---|
| Gln | Met | Tyr | Thr | Asp | Leu | Ser | Arg | Ser | Pro | Glu | Met | Asp | Gln | Glu | Pro | |
| | | | 190 | | | | | 195 | | | | | 200 | | | |

| ATC | GTC | TCA | CAC | CCG | AAG | CCT | GGG | AAA | GTC | CAC | AGT | AAT | ACC | TTT | CAG | 735 |
|---|---|---|---|---|---|---|---|---|---|---|---|---|---|---|---|---|
| Ile | Val | Ser | His | Pro | Lys | Pro | Gly | Lys | Val | His | Ser | Asn | Thr | Phe | Gln | |
| | | 205 | | | | | 210 | | | | | 215 | | | | |

| GAC | AGA | CTA | GGG | GTT | AGT | CAC | CTG | GGT | GAG | CAC | CAA | GGG | AAA | GGG | GCT | 783 |
|---|---|---|---|---|---|---|---|---|---|---|---|---|---|---|---|---|
| Asp | Arg | Leu | Gly | Val | Ser | His | Leu | Gly | Glu | His | Gln | Gly | Lys | Gly | Ala | |
| | 220 | | | | | 225 | | | | | 230 | | | | | |

| GTT | AGC | CAA | AAC | AAG | CCA | CAC | AAA | TCT | TCC | CAC | AAG | GAG | AAA | CGC | CCT | 831 |
|---|---|---|---|---|---|---|---|---|---|---|---|---|---|---|---|---|
| Val | Ser | Gln | Asn | Lys | Pro | His | Lys | Ser | Ser | His | Lys | Glu | Lys | Arg | Pro | |
| 235 | | | | | 240 | | | | | 245 | | | | | 250 | |

| GTG | GAT | GCC | AGG | GGG | GAT | GAG | AAG | AGC | TCT | GTC | ATG | GGC | AGA | GAG | AAG | 879 |
|---|---|---|---|---|---|---|---|---|---|---|---|---|---|---|---|---|
| Val | Asp | Ala | Arg | Gly | Asp | Glu | Lys | Ser | Ser | Val | Met | Gly | Arg | Glu | Lys | |
| | | | | 255 | | | | | 260 | | | | | 265 | | |

| TCA | CAC | AAA | GCC | TCT | TCC | AAA | GAG | GAG | AGC | CGA | AGG | CTA | CTC | TCA | GAG | 927 |
|---|---|---|---|---|---|---|---|---|---|---|---|---|---|---|---|---|
| Ser | His | Lys | Ala | Ser | Ser | Lys | Glu | Glu | Ser | Arg | Arg | Leu | Leu | Ser | Glu | |
| | | | 270 | | | | | 275 | | | | | 280 | | | |

| GAC | AGT | GCC | AAG | GAG | AAG | CTG | CCC | TCC | AGT | GTT | GTC | AAG | AAA | GAG | AAG | 975 |
|---|---|---|---|---|---|---|---|---|---|---|---|---|---|---|---|---|
| Asp | Ser | Ala | Lys | Glu | Lys | Leu | Pro | Ser | Ser | Val | Val | Lys | Lys | Glu | Lys | |
| | | 285 | | | | | 290 | | | | | 295 | | | | |

| | | | | | | | | | | | | | | | | |
|---|---|---|---|---|---|---|---|---|---|---|---|---|---|---|---|---|
| GAC | AGA | GAA | GGC | AAC | AGC | CTC | AAG | AAG | AAG | TTG | TCA | CCT | GCC | TTA | GAT | 1023 |
| Asp | Arg | Glu | Gly | Asn | Ser | Leu | Lys | Lys | Lys | Leu | Ser | Pro | Ala | Leu | Asp | |
| | 300 | | | | 305 | | | | | 310 | | | | | | |
| GTT | GCT | TCA | GAC | AAC | CAC | TTT | AAA | AAG | CCC | AAA | CAC | AAG | GAC | TCC | GAG | 1071 |
| Val | Ala | Ser | Asp | Asn | His | Phe | Lys | Lys | Pro | Lys | His | Lys | Asp | Ser | Glu | |
| 315 | | | | | 320 | | | | | 325 | | | | | 330 | |
| AAA | ATC | AAG | TCT | GAC | AAA | AAC | AAG | CAG | AGT | GTA | GAT | AGC | GTG | GAC | TCA | 1119 |
| Lys | Ile | Lys | Ser | Asp | Lys | Asn | Lys | Gln | Ser | Val | Asp | Ser | Val | Asp | Ser | |
| | | | | 335 | | | | | 340 | | | | | 345 | | |
| GGA | CGA | GGG | ACA | GGA | GAC | CCA | TTA | CCC | AGA | GCC | AAG | GAT | AAA | GTT | CCC | 1167 |
| Gly | Arg | Gly | Thr | Gly | Asp | Pro | Leu | Pro | Arg | Ala | Lys | Asp | Lys | Val | Pro | |
| | | | 350 | | | | | 355 | | | | | 360 | | | |
| AAC | AAC | CTG | AAG | GCT | CAG | GAG | GGG | AAA | GTA | AGA | ACT | AAC | TCG | GAT | CGA | 1215 |
| Asn | Asn | Leu | Lys | Ala | Gln | Glu | Gly | Lys | Val | Arg | Thr | Asn | Ser | Asp | Arg | |
| | | 365 | | | | | 370 | | | | | 375 | | | | |
| AAG | TCA | CCA | GGC | TCA | CTC | CCT | AAA | GTA | GAA | GAG | ATG | GAC | ATG | GAT | GAT | 1263 |
| Lys | Ser | Pro | Gly | Ser | Leu | Pro | Lys | Val | Glu | Glu | Met | Asp | Met | Asp | Asp | |
| | 380 | | | | | 385 | | | | | 390 | | | | | |
| GAG | TTT | GAG | CAG | CCC | ACC | ATG | TCC | TTT | GAG | TCA | TAC | CTC | AGC | TAT | GAC | 1311 |
| Glu | Phe | Glu | Gln | Pro | Thr | Met | Ser | Phe | Glu | Ser | Tyr | Leu | Ser | Tyr | Asp | |
| 395 | | | | | 400 | | | | | 405 | | | | | 410 | |
| CAG | CCC | CGC | AAG | AAA | AAG | AAG | AAG | GTT | GTG | AAA | ACT | TCC | GGT | ACA | GCA | 1359 |
| Gln | Pro | Arg | Lys | Lys | Lys | Lys | Lys | Val | Val | Lys | Thr | Ser | Gly | Thr | Ala | |
| | | | | 415 | | | | | 420 | | | | | 425 | | |
| CTT | GGA | GAA | AAA | GGA | CTT | AAA | AAG | AAG | GAC | TCT | AAA | AGC | ACT | AGT | AAA | 1407 |
| Leu | Gly | Glu | Lys | Gly | Leu | Lys | Lys | Lys | Asp | Ser | Lys | Ser | Thr | Ser | Lys | |
| | | | 430 | | | | | 435 | | | | | 440 | | | |
| AAC | TTG | AAC | TCG | GCT | CAG | AAA | TTA | CCC | AAG | GCG | AAT | GAA | AAC | AAG | TCA | 1455 |
| Asn | Leu | Asn | Ser | Ala | Gln | Lys | Leu | Pro | Lys | Ala | Asn | Glu | Asn | Lys | Ser | |
| | | 445 | | | | | 450 | | | | | 455 | | | | |
| GAC | AAG | TTG | CAG | CCA | GCT | GGA | GCC | GAA | CCC | ACG | AGG | CCT | AGA | AAG | GTC | 1503 |
| Asp | Lys | Leu | Gln | Pro | Ala | Gly | Ala | Glu | Pro | Thr | Arg | Pro | Arg | Lys | Val | |
| | 460 | | | | | 465 | | | | | 470 | | | | | |
| CCT | ACT | GAT | GTG | CTG | CCA | GCA | TTG | CCA | GAC | ATC | CCC | TTG | CCC | GCC | ATA | 1551 |
| Pro | Thr | Asp | Val | Leu | Pro | Ala | Leu | Pro | Asp | Ile | Pro | Leu | Pro | Ala | Ile | |
| 475 | | | | | 480 | | | | | 485 | | | | | 490 | |
| CAA | ACC | AAC | TAT | CGT | CCC | CTT | CCC | TCC | CTC | GAG | TTG | ATC | TCC | TCC | TTT | 1599 |
| Gln | Thr | Asn | Tyr | Arg | Pro | Leu | Pro | Ser | Leu | Glu | Leu | Ile | Ser | Ser | Phe | |
| | | | | 495 | | | | | 500 | | | | | 505 | | |
| CAG | CCA | AAG | CGA | AAA | GCT | TTC | TCT | TCA | CCC | CAG | GAA | GAA | GAA | GAA | GCT | 1647 |
| Gln | Pro | Lys | Arg | Lys | Ala | Phe | Ser | Ser | Pro | Gln | Glu | Glu | Glu | Glu | Ala | |
| | | | 510 | | | | | 515 | | | | | 520 | | | |
| GGG | TTC | ACA | GGA | CGC | AGA | ATG | AAT | TCT | AAG | ATG | CAG | GTG | TAT | TCA | GGT | 1695 |
| Gly | Phe | Thr | Gly | Arg | Arg | Met | Asn | Ser | Lys | Met | Gln | Val | Tyr | Ser | Gly | |
| | | 525 | | | | | 530 | | | | | 535 | | | | |
| TCC | AAG | TGT | GCC | TAT | CTC | CCC | AAA | ATG | ATG | ACC | TTG | CAC | CAG | CAG | TGT | 1743 |
| Ser | Lys | Cys | Ala | Tyr | Leu | Pro | Lys | Met | Met | Thr | Leu | His | Gln | Gln | Cys | |
| | 540 | | | | | 545 | | | | | 550 | | | | | |
| ATC | CGG | GTG | CTT | AAG | AAT | AAT | ATT | GAC | TCC | ATC | TTT | GAA | GTG | GGA | GGA | 1791 |
| Ile | Arg | Val | Leu | Lys | Asn | Asn | Ile | Asp | Ser | Ile | Phe | Glu | Val | Gly | Gly | |
| 555 | | | | | 560 | | | | | 565 | | | | | 570 | |
| GTC | CCC | TAT | TCT | GTT | CTT | GAA | CCT | GTC | TTG | GAG | AGG | TGC | ACA | CCC | GAT | 1839 |
| Val | Pro | Tyr | Ser | Val | Leu | Glu | Pro | Val | Leu | Glu | Arg | Cys | Thr | Pro | Asp | |
| | | | | 575 | | | | | 580 | | | | | 585 | | |
| CAG | CTC | TAC | CGA | ATA | GAG | GAA | TGC | AAT | CAT | GTA | TTA | ATT | GAG | GAA | ACA | 1887 |
| Gln | Leu | Tyr | Arg | Ile | Glu | Glu | Cys | Asn | His | Val | Leu | Ile | Glu | Glu | Thr | |
| | | | 590 | | | | | 595 | | | | | 600 | | | |
| GAT | CAG | TTG | TGG | AAA | GTT | CAC | TGT | CAC | CGG | GAC | TTT | AAG | GAA | GAA | AGA | 1935 |
| Asp | Gln | Leu | Trp | Lys | Val | His | Cys | His | Arg | Asp | Phe | Lys | Glu | Glu | Arg | |
| | | 605 | | | | | 610 | | | | | 615 | | | | |

| | | | | | | | | | | | | | | | | |
|---|---|---|---|---|---|---|---|---|---|---|---|---|---|---|---|---|
| CCA | GAA | GAG | TAT | GAG | TCT | TGG | AGG | GAG | ATG | TAC | CTG | AGG | CTT | CAG | GAC | 1983 |
| Pro | Glu | Glu | Tyr | Glu | Ser | Trp | Arg | Glu | Met | Tyr | Leu | Arg | Leu | Gln | Asp | |
| 620 | | | | | 625 | | | | | | 630 | | | | | |
| GCC | CGA | GAG | CAG | CGG | CTG | CGC | CTG | CTC | ACA | AAC | AAC | ATC | CGG | TCT | GCA | 2031 |
| Ala | Arg | Glu | Gln | Arg | Leu | Arg | Leu | Leu | Thr | Asn | Asn | Ile | Arg | Ser | Ala | |
| 635 | | | | 640 | | | | | 645 | | | | | | 650 | |
| CAT | GCC | AAT | AAG | CCA | AAA | GGA | CGA | CAA | GCA | AAG | ATG | GCC | TTT | GTG | AAC | 2079 |
| His | Ala | Asn | Lys | Pro | Lys | Gly | Arg | Gln | Ala | Lys | Met | Ala | Phe | Val | Asn | |
| | | | | 655 | | | | 660 | | | | | | 665 | | |
| TCT | GTG | GCC | AAG | CCA | CCG | AGA | GAT | GTT | CGA | CGG | AGG | CAG | GAG | AAG | TTT | 2127 |
| Ser | Val | Ala | Lys | Pro | Pro | Arg | Asp | Val | Arg | Arg | Arg | Gln | Glu | Lys | Phe | |
| | | | 670 | | | | 675 | | | | | 680 | | | | |
| GGA | ACC | GGG | GGA | GCA | GCT | GTC | CCT | GAG | AAA | GTC | AGG | ATT | AAG | CCA | GCA | 2175 |
| Gly | Thr | Gly | Gly | Ala | Ala | Val | Pro | Glu | Lys | Val | Arg | Ile | Lys | Pro | Ala | |
| | | 685 | | | | | 690 | | | | | 695 | | | | |
| CCA | TAT | ACA | ACA | GGA | AGC | AGC | CAT | GTT | CCT | GCC | AGC | AAC | AGC | AGC | AGC | 2223 |
| Pro | Tyr | Thr | Thr | Gly | Ser | Ser | His | Val | Pro | Ala | Ser | Asn | Ser | Ser | Ser | |
| | 700 | | | | | 705 | | | | | 710 | | | | | |
| AGC | TTC | CAC | TCA | AGT | CCT | GAG | GAG | CTG | GCC | TAC | GAA | GGG | CCC | AGT | ACC | 2271 |
| Ser | Phe | His | Ser | Ser | Pro | Glu | Glu | Leu | Ala | Tyr | Glu | Gly | Pro | Ser | Thr | |
| 715 | | | | | 720 | | | | | 725 | | | | | 730 | |
| AGC | AGT | GCC | CAC | TTA | GCT | CCT | GTG | GCC | AGC | AGC | TCT | GTT | TCC | TAT | GAT | 2319 |
| Ser | Ser | Ala | His | Leu | Ala | Pro | Val | Ala | Ser | Ser | Ser | Val | Ser | Tyr | Asp | |
| | | | | 735 | | | | | 740 | | | | | 745 | | |
| CCC | AGG | AAA | CCA | GCT | GTG | AAG | AAA | ATT | GCC | CCG | ATG | ATG | GCC | AAG | ACC | 2367 |
| Pro | Arg | Lys | Pro | Ala | Val | Lys | Lys | Ile | Ala | Pro | Met | Met | Ala | Lys | Thr | |
| | | | 750 | | | | | 755 | | | | | 760 | | | |
| ATT | AAA | GCA | TTC | AAG | AAC | AGA | TTT | TCC | CGA | CGA | TAA | ACAGGACTTG | | | | 2413 |
| Ile | Lys | Ala | Phe | Lys | Asn | Arg | Phe | Ser | Arg | Arg | * | | | | | |
| | | 765 | | | | | 770 | | | | | | | | | |

| | | | | |
|---|---|---|---|---|
| CCTTGGAGGT | TGAGTCTGGA | AGCAGGACTA | CAGGGACTAT | GGGGACGGGA | GAAGAGGATG | 2473 |
| TCCACAGAAG | ACCCGTATCT | TTTGCTCTGT | GGAACTTTTG | GCCTCTGACT | CCTGCACAGT | 2533 |
| TCCAGGTGTC | CCCCTCTGTG | CCTCAGCCCT | GCACCCTGCT | TGTAGCACAC | TAGTTTTAAT | 2593 |
| TAATAAATAT | TGCCCCCAGA | TGTATTTATA | ATACCCCAGG | GGTTTTTATT | TTATTTTATT | 2653 |
| TTCTCTTTGG | TCCACTATAT | TTAGCCTTCA | GATTCTGAAA | GACAGTATGA | GCCTCAGTCT | 2713 |
| TACTGAGGAC | TTTAAGATCA | GTTATACTTT | TGTTGCTAAT | TAGCATCTTT | GTAAACTATA | 2773 |
| AGACACTTTA | CTTTCCAGGT | CCTTTATTAA | AGTTAGATGA | GCCTAGCGAA | AGCCATTCTT | 2833 |
| GTCCTAGTCA | GCTCTTCTGA | GTAGACACTG | GTCCTTCAGA | GCCAGTGTGT | CACTCCAAAC | 2893 |
| CCAGATGCAG | GGCTAGGAGT | GAGTGAGTGC | CAGGATGCCT | GTCCTCCAGG | GGAGCCTCCC | 2953 |
| TGCTGAAACC | CCCACTGTTC | CTTGGTGGGC | ACTTTTACTT | CAGTAGATTT | GTTAAGGAAG | 3013 |
| GCCGTTTGCA | TCATCTTCAA | AGCATACTAC | TCTCCCCCAT | TTTCCAGCTC | ACTGGAGGAC | 3073 |
| AGAGCCTAAG | AGATGAACTG | ATGTAGGACC | TCAGCAGTTT | TATAATTTTA | GTTTCTGGTT | 3133 |
| CAGTATTTTA | CACACAGACA | GACACACAGA | CACACAGACC | CTTCCTTATT | TTGTCTCTCC | 3193 |
| CTGCACTGTG | GGGAAACACA | CATGACAGGG | CTTTTGTAGC | TCTGATGTGG | TTGGGGGGTT | 3253 |
| TGAAAAGCCA | GCACTTTATT | TCCTTGTTCT | CTATGAATTC | CTACCAGGAG | TGAGTGGTTT | 3313 |
| AGAGCATTGT | AGTGCTGTGA | AGCTTGCTCG | TGTTGGACAG | GAAAGGTGCT | GACGTGGCCA | 3373 |
| GAGGAGCAGC | AGTGCACTGT | AGCCAGCAGA | GAACTCTGTG | AAGCCTCCGC | CTTCTGAGTG | 3433 |
| TTGGCCAGAG | TTAGGGATGG | GCCACCTGCC | GAAGGGTAGA | TGGTCACCCT | GGTCCCAGCC | 3493 |
| AGTCAGTT | | | | | | 3501 |

( 2 ) INFORMATION FOR SEQ ID NO:6:

( i ) SEQUENCE CHARACTERISTICS:
    ( A ) LENGTH: 773 amino acids
    ( B ) TYPE: amino acid
    ( D ) TOPOLOGY: linear ( i i ) MOLECULE TYPE: protein ( x i ) SEQUENCE DESCRIPTION: SEQ ID NO:6:

```
Met Ala Ala Glu Ser Ala Leu Gln Val Val Glu Lys Leu Gln Ala Arg
 1               5                  10                  15

Leu Ala Ala Asn Pro Asp Pro Lys Lys Leu Leu Lys Tyr Leu Lys Lys
                20                  25                  30

Leu Ser Val Leu Pro Ile Thr Val Asp Ile Leu Val Glu Thr Gly Val
            35                  40                  45

Gly Lys Thr Val Asn Ser Phe Arg Lys His Glu Gln Val Gly Asn Phe
        50                  55                  60

Ala Arg Asp Leu Val Ala Gln Trp Lys Lys Leu Val Pro Val Glu Arg
65                  70                  75                  80

Asn Asn Glu Ala Glu Asp Gln Asp Phe Glu Lys Ser Asn Ser Arg Lys
                85                  90                  95

Arg Pro Arg Asp Val Pro Gln Gln Glu Glu Glu Ala Glu Gly Asn Tyr
                100                 105                 110

Gln Glu Ser Trp Gln Ala Ser Gly Ser Gln Pro Tyr Ser Pro Glu His
            115                 120                 125

Arg Gln Lys Lys His Arg Lys Leu Pro Glu Leu Glu Arg Pro His Lys
        130                 135                 140

Val Ala His Gly His Glu Arg Arg Asp Glu Arg Lys Arg Cys His Lys
145                 150                 155                 160

Val Ser Pro Pro Tyr Ser Ser Asp Pro Glu Ser Ser Asp Tyr Gly His
                165                 170                 175

Val Gln Ser Pro Pro Ser Ser Pro His Gln Met Tyr Thr Asp Leu
            180                 185                 190

Ser Arg Ser Pro Glu Met Asp Gln Glu Pro Ile Val Ser His Pro Lys
        195                 200                 205

Pro Gly Lys Val His Ser Asn Thr Phe Gln Asp Arg Leu Gly Val Ser
    210                 215                 220

His Leu Gly Glu His Gln Gly Lys Gly Ala Val Ser Gln Asn Lys Pro
225                 230                 235                 240

His Lys Ser Ser His Lys Glu Lys Arg Pro Val Asp Ala Arg Gly Asp
                245                 250                 255

Glu Lys Ser Ser Val Met Gly Arg Glu Lys Ser His Lys Ala Ser Ser
            260                 265                 270

Lys Glu Glu Ser Arg Arg Leu Leu Ser Glu Asp Ser Ala Lys Glu Lys
        275                 280                 285

Leu Pro Ser Ser Val Val Lys Lys Glu Lys Asp Arg Glu Gly Asn Ser
    290                 295                 300

Leu Lys Lys Lys Leu Ser Pro Ala Leu Asp Val Ala Ser Asp Asn His
305                 310                 315                 320

Phe Lys Lys Pro Lys His Lys Asp Ser Glu Lys Ile Lys Ser Asp Lys
                325                 330                 335

Asn Lys Gln Ser Val Asp Ser Val Asp Ser Gly Arg Gly Thr Gly Asp
            340                 345                 350

Pro Leu Pro Arg Ala Lys Asp Lys Val Pro Asn Asn Leu Lys Ala Gln
        355                 360                 365

Glu Gly Lys Val Arg Thr Asn Ser Asp Arg Lys Ser Pro Gly Ser Leu
```

|     |     |     | 370 |     |     | 375 |     |     |     | 380 |     |     |
| --- | --- | --- | --- | --- | --- | --- | --- | --- | --- | --- | --- | --- |
| Pro | Lys | Val | Glu | Glu | Met | Asp | Met | Asp | Asp | Glu | Phe | Glu | Gln | Pro | Thr |
| 385 |     |     |     |     | 390 |     |     |     | 395 |     |     |     |     |     | 400 |
| Met | Ser | Phe | Glu | Ser | Tyr | Leu | Ser | Tyr | Asp | Gln | Pro | Arg | Lys | Lys | Lys |
|     |     |     |     | 405 |     |     |     |     | 410 |     |     |     | 415 |     |     |
| Lys | Lys | Val | Val | Lys | Thr | Ser | Gly | Thr | Ala | Leu | Gly | Glu | Lys | Gly | Leu |
|     |     |     | 420 |     |     |     |     | 425 |     |     |     |     | 430 |     |     |
| Lys | Lys | Lys | Asp | Ser | Lys | Ser | Thr | Ser | Lys | Asn | Leu | Asn | Ser | Ala | Gln |
|     |     | 435 |     |     |     |     | 440 |     |     |     |     | 445 |     |     |     |
| Lys | Leu | Pro | Lys | Ala | Asn | Glu | Asn | Lys | Ser | Asp | Lys | Leu | Gln | Pro | Ala |
|     | 450 |     |     |     |     | 455 |     |     |     |     | 460 |     |     |     |     |
| Gly | Ala | Glu | Pro | Thr | Arg | Pro | Arg | Lys | Val | Pro | Thr | Asp | Val | Leu | Pro |
| 465 |     |     |     |     | 470 |     |     |     |     | 475 |     |     |     |     | 480 |
| Ala | Leu | Pro | Asp | Ile | Pro | Leu | Pro | Ala | Ile | Gln | Thr | Asn | Tyr | Arg | Pro |
|     |     |     |     | 485 |     |     |     |     | 490 |     |     |     |     | 495 |     |
| Leu | Pro | Ser | Leu | Glu | Leu | Ile | Ser | Ser | Phe | Gln | Pro | Lys | Arg | Lys | Ala |
|     |     |     | 500 |     |     |     |     | 505 |     |     |     |     | 510 |     |     |
| Phe | Ser | Ser | Pro | Gln | Glu | Glu | Glu | Ala | Gly | Phe | Thr | Gly | Arg | Arg |
|     |     | 515 |     |     |     |     | 520 |     |     |     |     | 525 |     |     |     |
| Met | Asn | Ser | Lys | Met | Gln | Val | Tyr | Ser | Gly | Ser | Lys | Cys | Ala | Tyr | Leu |
|     | 530 |     |     |     |     | 535 |     |     |     |     | 540 |     |     |     |     |
| Pro | Lys | Met | Met | Thr | Leu | His | Gln | Gln | Cys | Ile | Arg | Val | Leu | Lys | Asn |
| 545 |     |     |     |     | 550 |     |     |     |     | 555 |     |     |     |     | 560 |
| Asn | Ile | Asp | Ser | Ile | Phe | Glu | Val | Gly | Gly | Val | Pro | Tyr | Ser | Val | Leu |
|     |     |     |     | 565 |     |     |     |     | 570 |     |     |     |     | 575 |     |
| Glu | Pro | Val | Leu | Glu | Arg | Cys | Thr | Pro | Asp | Gln | Leu | Tyr | Arg | Ile | Glu |
|     |     |     | 580 |     |     |     |     | 585 |     |     |     |     | 590 |     |     |
| Glu | Cys | Asn | His | Val | Leu | Ile | Glu | Glu | Thr | Asp | Gln | Leu | Trp | Lys | Val |
|     |     | 595 |     |     |     |     | 600 |     |     |     |     | 605 |     |     |     |
| His | Cys | His | Arg | Asp | Phe | Lys | Glu | Glu | Arg | Pro | Glu | Glu | Tyr | Glu | Ser |
|     | 610 |     |     |     |     | 615 |     |     |     |     | 620 |     |     |     |     |
| Trp | Arg | Glu | Met | Tyr | Leu | Arg | Leu | Gln | Asp | Ala | Arg | Glu | Gln | Arg | Leu |
| 625 |     |     |     |     | 630 |     |     |     |     | 635 |     |     |     |     | 640 |
| Arg | Leu | Leu | Thr | Asn | Asn | Ile | Arg | Ser | Ala | His | Ala | Asn | Lys | Pro | Lys |
|     |     |     |     | 645 |     |     |     |     | 650 |     |     |     |     | 655 |     |
| Gly | Arg | Gln | Ala | Lys | Met | Ala | Phe | Val | Asn | Ser | Val | Ala | Lys | Pro | Pro |
|     |     |     | 660 |     |     |     |     | 665 |     |     |     |     | 670 |     |     |
| Arg | Asp | Val | Arg | Arg | Arg | Gln | Glu | Lys | Phe | Gly | Thr | Gly | Gly | Ala | Ala |
|     |     |     | 675 |     |     |     |     | 680 |     |     |     |     | 685 |     |     |
| Val | Pro | Glu | Lys | Val | Arg | Ile | Lys | Pro | Ala | Pro | Tyr | Thr | Thr | Gly | Ser |
|     |     | 690 |     |     |     |     | 695 |     |     |     |     | 700 |     |     |     |
| Ser | His | Val | Pro | Ala | Ser | Asn | Ser | Ser | Ser | Ser | Phe | His | Ser | Ser | Pro |
| 705 |     |     |     |     | 710 |     |     |     |     | 715 |     |     |     |     | 720 |
| Glu | Glu | Leu | Ala | Tyr | Glu | Gly | Pro | Ser | Thr | Ser | Ser | Ala | His | Leu | Ala |
|     |     |     |     | 725 |     |     |     |     | 730 |     |     |     |     | 735 |     |
| Pro | Val | Ala | Ser | Ser | Ser | Val | Ser | Tyr | Asp | Pro | Arg | Lys | Pro | Ala | Val |
|     |     |     | 740 |     |     |     |     | 745 |     |     |     |     | 750 |     |     |
| Lys | Lys | Ile | Ala | Pro | Met | Met | Ala | Lys | Thr | Ile | Lys | Ala | Phe | Lys | Asn |
|     |     | 755 |     |     |     |     | 760 |     |     |     |     | 765 |     |     |     |
| Arg | Phe | Ser | Arg | Arg |
|     |     | 770 |     |     |

( 2 ) INFORMATION FOR SEQ ID NO:7:

( i ) SEQUENCE CHARACTERISTICS:
    ( A ) LENGTH: 444 base pairs
    ( B ) TYPE: nucleic acid
    ( C ) STRANDEDNESS: both
    ( D ) TOPOLOGY: both ( i i ) MOLECULE TYPE: cDNA to mRNA ( v i ) ORIGINAL SOURCE:
    ( A ) ORGANISM: Homo sapiens
    ( F ) TISSUE TYPE: Blood
    ( G ) CELL TYPE: Lymphocyte ( i x ) FEATURE:
    ( A ) NAME/KEY: CDS
    ( B ) LOCATION: 88..426

( x i ) SEQUENCE DESCRIPTION: SEQ ID NO:7:

```
AGATTTGGCA CGAGTCGGCA CGAGGCGGGA CTGACGAGAA ACTACTAAAG TTCCTGGGGA      60

AGCAAAGTAG AATTTCATAA GAACAAA ATG GAT GGA GAG GAG AAA ACC TAT        111
                              Met Asp Gly Glu Glu Lys Thr Tyr
                               1                   5

GGT GGC TGT GAA GGA CCT GAT GCC ATG TAT GTC AAA TTG ATA TCA TCT      159
Gly Gly Cys Glu Gly Pro Asp Ala Met Tyr Val Lys Leu Ile Ser Ser
 10               15                  20

GAT GGC CAT GAA TTT ATT GTA AAA AGA GAA CAT GCA TTA ACA TCA GGC      207
Asp Gly His Glu Phe Ile Val Lys Arg Glu His Ala Leu Thr Ser Gly
 25              30                  35                  40

ACG ATA AAA GCC ATG TTG AGT GGC CCA GGT CAG TTT GCT GAG AAC GAA      255
Thr Ile Lys Ala Met Leu Ser Gly Pro Gly Gln Phe Ala Glu Asn Glu
                 45                  50                  55

ACC AAT GAG GTC AAT TTT AGA GAG ATA CCT TCA CAT GTG CTA TCG AAA      303
Thr Asn Glu Val Asn Phe Arg Glu Ile Pro Ser His Val Leu Ser Lys
             60                  65                  70

GTA TGC ATG TAT TTT ACG TAC AAG GTT CGC TAC ACT AAC AGC TCC ACC      351
Val Cys Met Tyr Phe Thr Tyr Lys Val Arg Tyr Thr Asn Ser Ser Thr
         75                  80                  85

GAG ATT CCT GAA TTC CCA ATT GCA CCT GAA ATT GCA CTG GAA CTG CTG      399
Glu Ile Pro Glu Phe Pro Ile Ala Pro Glu Ile Ala Leu Glu Leu Leu
     90                  95                 100

ATG GCT GCG AAC TTC TTA GAT TGT TAA ATAAATAAA TTATAATA               444
Met Ala Ala Asn Phe Leu Asp Cys *
105                 110
```

( 2 ) INFORMATION FOR SEQ ID NO:8:

( i ) SEQUENCE CHARACTERISTICS:
        ( A ) LENGTH: 112 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Asp Gly Glu Glu Lys Thr Tyr Gly Gly Cys Glu Gly Pro Asp Ala
 1               5                  10                  15

Met Tyr Val Lys Leu Ile Ser Ser Asp Gly His Glu Phe Ile Val Lys
                 20                  25                  30

Arg Glu His Ala Leu Thr Ser Gly Thr Ile Lys Ala Met Leu Ser Gly
             35                  40                  45

Pro Gly Gln Phe Ala Glu Asn Glu Thr Asn Glu Val Asn Phe Arg Glu
         50                  55                  60

Ile Pro Ser His Val Leu Ser Lys Val Cys Met Tyr Phe Thr Tyr Lys
 65                  70                  75                  80
```

```
Val Arg Tyr Thr Asn Ser Ser Thr Glu Ile Pro Glu Phe Pro Ile Ala
             85                  90                  95

Pro Glu Ile Ala Leu Glu Leu Leu Met Ala Ala Asn Phe Leu Asp Cys
            100                 105                 110
```

( 2 ) INFORMATION FOR SEQ ID NO:9:

( i ) SEQUENCE CHARACTERISTICS:
        ( A ) LENGTH: 357 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 1..357

( x i ) SEQUENCE DESCRIPTION: SEQ ID NO:9:

```
ATG GAC GTG TTC CTC ATG ATC CGG CGC CAC AAG ACC ACC ATC TTC ACG    48
Met Asp Val Phe Leu Met Ile Arg Arg His Lys Thr Thr Ile Phe Thr
1               5                   10                  15

GAC GCC AAG GAG TCC AGC ACG GTG TTC GAA CTG AAG CGC ATC GTC GAG    96
Asp Ala Lys Glu Ser Ser Thr Val Phe Glu Leu Lys Arg Ile Val Glu
                20                  25                  30

GGC ATC CTC AAG CGG CCT CCT GAC GAG CAG CGG CTG TAC AAG GAT GAC   144
Gly Ile Leu Lys Arg Pro Pro Asp Glu Gln Arg Leu Tyr Lys Asp Asp
            35                  40                  45

CAA CTC TTG GAT GAT GGC AAG ACA CTG GGC GAG TGT GGC TTC ACC AGT   192
Gln Leu Leu Asp Asp Gly Lys Thr Leu Gly Glu Cys Gly Phe Thr Ser
        50                  55                  60

CAA ACA GCA CGG CCA CAG GCC CCA GCC ACA GTG GGG CTG GCC TTC CGG   240
Gln Thr Ala Arg Pro Gln Ala Pro Ala Thr Val Gly Leu Ala Phe Arg
65                  70                  75                  80

GCA GAT GAC ACC TTT GAG GCC CTG TGC ATC GAG CCG TTT TCC AGC CCG   288
Ala Asp Asp Thr Phe Glu Ala Leu Cys Ile Glu Pro Phe Ser Ser Pro
                85                  90                  95

CCA GAG CTG CCC GAT GTG ATG AAG CCC CAG GAC TCG GGA AGC AGT GCC   336
Pro Glu Leu Pro Asp Val Met Lys Pro Gln Asp Ser Gly Ser Ser Ala
            100                 105                 110

AAT GAA CAA GCC GTG CAG TGA                                       357
Asn Glu Gln Ala Val Gln *
        115
```

( 2 ) INFORMATION FOR SEQ ID NO:10:

( i ) SEQUENCE CHARACTERISTICS:
        ( A ) LENGTH: 118 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Asp Val Phe Leu Met Ile Arg Arg His Lys Thr Thr Ile Phe Thr
1               5                   10                  15

Asp Ala Lys Glu Ser Ser Thr Val Phe Glu Leu Lys Arg Ile Val Glu
                20                  25                  30

Gly Ile Leu Lys Arg Pro Pro Asp Glu Gln Arg Leu Tyr Lys Asp Asp
            35                  40                  45

Gln Leu Leu Asp Asp Gly Lys Thr Leu Gly Glu Cys Gly Phe Thr Ser
        50                  55                  60

Gln Thr Ala Arg Pro Gln Ala Pro Ala Thr Val Gly Leu Ala Phe Arg
```

```
              65                         70                        75                          80
Ala  Asp  Asp  Thr  Phe  Glu  Ala  Leu  Cys  Ile  Glu  Pro  Phe  Ser  Ser  Pro
                         85                        90                        95

Pro  Glu  Leu  Pro  Asp  Val  Met  Lys  Pro  Gln  Asp  Ser  Gly  Ser  Ser  Ala
               100                      105                      110

Asn  Glu  Gln  Ala  Val  Gln
               115
```

( 2 ) INFORMATION FOR SEQ ID NO:11:

( i ) SEQUENCE CHARACTERISTICS:
        ( A ) LENGTH: 2690 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 33..2351

( x i ) SEQUENCE DESCRIPTION: SEQ ID NO:11:

```
GTTCCGGCGA  GGAGGCCGCG  CCAGTGACAG  CG  ATG  GCG  GCG  GAG  TCG  GCG  CTC        53
                                        Met  Ala  Ala  Glu  Ser  Ala  Leu
                                         1                 5

CAA  GTT  GTG  GAG  AAG  CTG  CAG  GCG  CGC  CTG  GCC  GCG  AAC  CCG  GAC  CCT   101
Gln  Val  Val  Glu  Lys  Leu  Gln  Ala  Arg  Leu  Ala  Ala  Asn  Pro  Asp  Pro
               10                        15                        20

AAG  AAG  CTA  TTG  AAA  TAT  TTG  AAG  AAA  CTC  TCC  ACC  CTG  CCT  ATT  ACA   149
Lys  Lys  Leu  Leu  Lys  Tyr  Leu  Lys  Lys  Leu  Ser  Thr  Leu  Pro  Ile  Thr
     25                        30                        35

GTA  GAC  ATT  CTT  GCG  GAG  ACT  GGG  GTT  GGG  AAA  ACA  GTA  AAT  AGC  TTG   197
Val  Asp  Ile  Leu  Ala  Glu  Thr  Gly  Val  Gly  Lys  Thr  Val  Asn  Ser  Leu
40                       45                        50                        55

CGA  AAA  CAC  GAG  CAT  GTT  GGA  AGC  TTT  GCC  AGG  GAC  CTA  GTG  GCC  CAG   245
Arg  Lys  His  Glu  His  Val  Gly  Ser  Phe  Ala  Arg  Asp  Leu  Val  Ala  Gln
                    60                        65                        70

TGG  AAG  AAG  CTG  GTT  CCT  GTG  GAA  CGA  AAT  GCT  GAG  CCT  GAT  GAA  CAG   293
Trp  Lys  Lys  Leu  Val  Pro  Val  Glu  Arg  Asn  Ala  Glu  Pro  Asp  Glu  Gln
               75                        80                        85

GAC  TTT  GAG  AAG  AGC  AAT  TCC  CGA  AAG  CGC  CCT  CGG  GAT  GCC  CTG  CAG   341
Asp  Phe  Glu  Lys  Ser  Asn  Ser  Arg  Lys  Arg  Pro  Arg  Asp  Ala  Leu  Gln
          90                        95                       100

AAG  GAG  GAG  GAG  ATG  GAG  GGG  GAC  TAC  CAA  GAA  ACC  TGG  AAA  GCC  ACG   389
Lys  Glu  Glu  Glu  Met  Glu  Gly  Asp  Tyr  Gln  Glu  Thr  Trp  Lys  Ala  Thr
     105                      110                      115

GGG  AGC  CGA  TCC  TAT  AGC  CCT  GAC  CAC  AGG  CAG  AAG  AAA  CAT  AGG  AAA   437
Gly  Ser  Arg  Ser  Tyr  Ser  Pro  Asp  His  Arg  Gln  Lys  Lys  His  Arg  Lys
120                      125                      130                      135

CTC  TCG  GAG  CTC  GAG  AGA  CCT  CAC  AAA  GTG  TCT  CAC  GGT  CAT  GAG  AGG   485
Leu  Ser  Glu  Leu  Glu  Arg  Pro  His  Lys  Val  Ser  His  Gly  His  Glu  Arg
                    140                      145                      150

AGA  GAT  GAG  AGA  AAG  AGG  TGT  CAC  AGA  ATG  TCA  CCA  ACT  TAC  TCT  TCA   533
Arg  Asp  Glu  Arg  Lys  Arg  Cys  His  Arg  Met  Ser  Pro  Thr  Tyr  Ser  Ser
               155                      160                      165

GAC  CCT  GAG  TCT  TCT  GAT  TAT  GGC  CAT  GTT  CAA  TCC  CCT  CCA  TCT  TGT   581
Asp  Pro  Glu  Ser  Ser  Asp  Tyr  Gly  His  Val  Gln  Ser  Pro  Pro  Ser  Cys
          170                      175                      180

ACC  AGT  CCT  CAT  CAG  ATG  TAC  GTC  GAC  CAC  TAC  AGA  TCC  CTG  GAG  GAG   629
Thr  Ser  Pro  His  Gln  Met  Tyr  Val  Asp  His  Tyr  Arg  Ser  Leu  Glu  Glu
     185                      190                      195
```

```
GAC CAG GAG CCC ATT GTT TCA CAC CAG AAG CCT GGG AAA GGC CAC AGC    677
Asp Gln Glu Pro Ile Val Ser His Gln Lys Pro Gly Lys Gly His Ser
200             205             210             215

AAT GCC TTT CAG GAC AGA CTC GGG GCC AGC CAA GAA CGA CAC CTG GGT    725
Asn Ala Phe Gln Asp Arg Leu Gly Ala Ser Gln Glu Arg His Leu Gly
                220             225             230

GAA CCC CAT GGG AAA GGG GTT GTG AGT CAA AAC AAG GAG CAC AAA TCT    773
Glu Pro His Gly Lys Gly Val Val Ser Gln Asn Lys Glu His Lys Ser
            235             240             245

TCC CAC AAG GAC AAA CGC CCC GTG GAT GCC AAG AGT GAT GAG AAG GCC    821
Ser His Lys Asp Lys Arg Pro Val Asp Ala Lys Ser Asp Glu Lys Ala
        250             255             260

TCT GTG GTG AGC AGA GAG AAA TCA CAC AAG GCC CTC TCC AAA GAG GAG    869
Ser Val Val Ser Arg Glu Lys Ser His Lys Ala Leu Ser Lys Glu Glu
    265             270             275

AAC CGA AGG CCA CCC TCA GGG GAC AAT GCA AGG GAG AAA CCG CCC TCT    917
Asn Arg Arg Pro Pro Ser Gly Asp Asn Ala Arg Glu Lys Pro Pro Ser
280             285             290             295

AGT GGC GTA AAG AAA GAG AAG GAC AGA GAG GGC AGC AGC CTG AAG AAG    965
Ser Gly Val Lys Lys Glu Lys Asp Arg Glu Gly Ser Ser Leu Lys Lys
                300             305             310

AAG TGT TTG CCT CCC TCA GAG GCC GCT TCA GAC AAC CAC CTG AAA AAG   1013
Lys Cys Leu Pro Pro Ser Glu Ala Ala Ser Asp Asn His Leu Lys Lys
            315             320             325

CCA AAG CAC AGA GAC CCA GAG AAA GCC AAA TTG GAC AAA AGC AAG CAA   1061
Pro Lys His Arg Asp Pro Glu Lys Ala Lys Leu Asp Lys Ser Lys Gln
        330             335             340

GGT CTG GAC AGC TTT GAC ACA GGA AAA GGA GCA GGA GAC CTG TTG CCC   1109
Gly Leu Asp Ser Phe Asp Thr Gly Lys Gly Ala Gly Asp Leu Leu Pro
    345             350             355

AAG GTA AAA GAG AAG GGT TCT AAC AAC CTA AAG ACT CCA GAA GGG AAA   1157
Lys Val Lys Glu Lys Gly Ser Asn Asn Leu Lys Thr Pro Glu Gly Lys
360             365             370             375

GTC AAA ACT AAT TTG GAT AGA AAG TCA CTG GGC TCC CTC CCT AAA GTT   1205
Val Lys Thr Asn Leu Asp Arg Lys Ser Leu Gly Ser Leu Pro Lys Val
                380             385             390

GAG GAG ACA GAT ATG GAG GAT GAA TTC GAG CAG CCA ACC ATG TCT TTT   1253
Glu Glu Thr Asp Met Glu Asp Glu Phe Glu Gln Pro Thr Met Ser Phe
            395             400             405

GAA TCC TAC CTC AGC TAT GAC CAG CCC CGG AAG AAA AAG AAA AAG ATT   1301
Glu Ser Tyr Leu Ser Tyr Asp Gln Pro Arg Lys Lys Lys Lys Lys Ile
        410             415             420

GTG AAA ACT TCA GCC ACG GCA CTT GGA GAT AAA GGA CTT AAA AAA AAT   1349
Val Lys Thr Ser Ala Thr Ala Leu Gly Asp Lys Gly Leu Lys Lys Asn
    425             430             435

GAC TCT AAA AGC ACT GGT AAA AAC TTG GAC TCA GTT CAG AAA TTA CCC   1397
Asp Ser Lys Ser Thr Gly Lys Asn Leu Asp Ser Val Gln Lys Leu Pro
440             445             450             455

AAG GTG AAC AAA ACC AAG TCA GAG AAG CCG GCT GGA GCT GAT TTA GCC   1445
Lys Val Asn Lys Thr Lys Ser Glu Lys Pro Ala Gly Ala Asp Leu Ala
                460             465             470

AAG CTG AGA AAG GTG CCT GAT GTG TTG CCA GTG TTG CCA GAC CTC CCG   1493
Lys Leu Arg Lys Val Pro Asp Val Leu Pro Val Leu Pro Asp Leu Pro
            475             480             485

TTA CCC GCG ATA CAG GCC AAT TAC CGT CCA CTG CCT TCC CTC GAG CTG   1541
Leu Pro Ala Ile Gln Ala Asn Tyr Arg Pro Leu Pro Ser Leu Glu Leu
        490             495             500

ATA TCC TCC TTC CAG CCA AAG CGA AAA GCG TTC TCT TCA CCC CAG GAA   1589
Ile Ser Ser Phe Gln Pro Lys Arg Lys Ala Phe Ser Ser Pro Gln Glu
    505             510             515
```

| | | | | | | | | | | | | | | | | |
|---|---|---|---|---|---|---|---|---|---|---|---|---|---|---|---|---|
| GAA | GAA | GAA | GCT | GGA | TTT | ACT | GGG | CGC | AGA | ATG | AAT | TCC | AAG | ATG | CAG | 1637 |
| Glu | Glu | Glu | Ala | Gly | Phe | Thr | Gly | Arg | Arg | Met | Asn | Ser | Lys | Met | Gln | |
| 520 | | | | 525 | | | | | 530 | | | | | | 535 | |
| GTG | TAT | TCT | GGT | TCC | AAG | TGT | GCC | TAT | CTC | CCT | AAA | ATG | ATG | ACC | TTG | 1685 |
| Val | Tyr | Ser | Gly | Ser | Lys | Cys | Ala | Tyr | Leu | Pro | Lys | Met | Met | Thr | Leu | |
| | | | | 540 | | | | | 545 | | | | | 550 | | |
| CAC | CAG | CAA | TGC | ATC | CGA | GTA | CTT | AAA | AAC | AAC | ATC | GAT | TCA | ATC | TTT | 1733 |
| His | Gln | Gln | Cys | Ile | Arg | Val | Leu | Lys | Asn | Asn | Ile | Asp | Ser | Ile | Phe | |
| | | | 555 | | | | | 560 | | | | | 565 | | | |
| GAA | GTG | GGA | GGA | GTC | CCA | TAC | TCT | GTT | CTT | GAA | CCC | GTT | TTG | GAG | AGG | 1781 |
| Glu | Val | Gly | Gly | Val | Pro | Tyr | Ser | Val | Leu | Glu | Pro | Val | Leu | Glu | Arg | |
| | | 570 | | | | | 575 | | | | | 580 | | | | |
| TGT | ACA | CCT | GAT | CAG | CTG | TAT | CGC | ATA | GAG | GAA | TAC | AAT | CAT | GTA | TTA | 1829 |
| Cys | Thr | Pro | Asp | Gln | Leu | Tyr | Arg | Ile | Glu | Glu | Tyr | Asn | His | Val | Leu | |
| | 585 | | | | | 590 | | | | | 595 | | | | | |
| ATT | GAA | GAA | ACA | GAT | CAA | TTA | TGG | AAA | GTT | CAT | TGT | CAC | CGA | GAC | TTT | 1877 |
| Ile | Glu | Glu | Thr | Asp | Gln | Leu | Trp | Lys | Val | His | Cys | His | Arg | Asp | Phe | |
| 600 | | | | | 605 | | | | | 610 | | | | | 615 | |
| AAG | GAA | GAA | AGA | CCC | GAA | GAG | TAT | GAG | TCG | TGG | CGA | GAG | ATG | TAC | CTG | 1925 |
| Lys | Glu | Glu | Arg | Pro | Glu | Glu | Tyr | Glu | Ser | Trp | Arg | Glu | Met | Tyr | Leu | |
| | | | | 620 | | | | | 625 | | | | | 630 | | |
| CGG | CTT | CAG | GAC | GCC | CGA | GAG | CAG | CGG | CTA | CGA | GTA | CTA | ACA | AAG | AAT | 1973 |
| Arg | Leu | Gln | Asp | Ala | Arg | Glu | Gln | Arg | Leu | Arg | Val | Leu | Thr | Lys | Asn | |
| | | | 635 | | | | | 640 | | | | | 645 | | | |
| ATC | CAG | TTC | GCA | CAT | GCC | AAT | AAG | CCC | AAA | GGC | CGA | CAA | GCA | AAG | ATG | 2021 |
| Ile | Gln | Phe | Ala | His | Ala | Asn | Lys | Pro | Lys | Gly | Arg | Gln | Ala | Lys | Met | |
| | | 650 | | | | | 655 | | | | | 660 | | | | |
| GCC | TTT | GTC | AAC | TCT | GTG | GCC | AAG | CCA | CCT | CGT | GAC | GTC | CGG | AGG | AGG | 2069 |
| Ala | Phe | Val | Asn | Ser | Val | Ala | Lys | Pro | Pro | Arg | Asp | Val | Arg | Arg | Arg | |
| | 665 | | | | | 670 | | | | | 675 | | | | | |
| CAG | GAA | AAG | TTT | GGA | ACG | GGA | GGA | GCA | GCT | GTC | CCT | GAG | AAA | ATC | AAG | 2117 |
| Gln | Glu | Lys | Phe | Gly | Thr | Gly | Gly | Ala | Ala | Val | Pro | Glu | Lys | Ile | Lys | |
| 680 | | | | | 685 | | | | | 690 | | | | | 695 | |
| ATC | AAG | CCA | GCC | CCG | TAC | CCC | ATG | GGA | AGC | AGC | CAT | GCT | TCC | GCC | AGT | 2165 |
| Ile | Lys | Pro | Ala | Pro | Tyr | Pro | Met | Gly | Ser | Ser | His | Ala | Ser | Ala | Ser | |
| | | | | 700 | | | | | 705 | | | | | 710 | | |
| AGC | ATC | AGC | TTT | AAC | CCC | AGC | CCT | GAG | GAG | CCG | GCC | TAT | GAT | GGC | CCA | 2213 |
| Ser | Ile | Ser | Phe | Asn | Pro | Ser | Pro | Glu | Glu | Pro | Ala | Tyr | Asp | Gly | Pro | |
| | | | 715 | | | | | 720 | | | | | 725 | | | |
| AGC | ACC | AGC | AGT | GCC | CAC | TTG | GCA | CCA | GTG | GTC | AGC | AGC | ACT | GTT | TCC | 2261 |
| Ser | Thr | Ser | Ser | Ala | His | Leu | Ala | Pro | Val | Val | Ser | Ser | Thr | Val | Ser | |
| | | 730 | | | | | 735 | | | | | 740 | | | | |
| TAT | GAT | CCT | AGG | AAA | CCC | ACT | GTG | AAG | AAA | ATT | GCC | CCA | ATG | ATG | GCC | 2309 |
| Tyr | Asp | Pro | Arg | Lys | Pro | Thr | Val | Lys | Lys | Ile | Ala | Pro | Met | Met | Ala | |
| | 745 | | | | | 750 | | | | | 755 | | | | | |
| AAG | ACA | ATT | AAA | GCT | TTC | AAG | AAC | AGA | TTC | TCC | CGA | CGA | TAA | | | 2351 |
| Lys | Thr | Ile | Lys | Ala | Phe | Lys | Asn | Arg | Phe | Ser | Arg | Arg | * | | | |
| 760 | | | | 765 | | | | | 770 | | | | | | | |

| | | | | |
|---|---|---|---|---|
| ACTGAGGACT | TGCCTTGGAA | ATGGAATCTG | GGGAGGCAGG | AATACAAGGA | CAGTGGGGGT | 2411 |
| TGGGGAATGG | AATTCTACAG | GAGACTGGAG | TCTTGCTTTG | TGGATCCTTT | TGGTCTCCGA | 2471 |
| GTCTGCAGTC | TGCAGGTGCT | GCCCCTGGGA | ACCTGCGTGC | CACAGCCCCG | CCTCCCTGCC | 2531 |
| TGGAGCACAC | TTTAGAATTC | TGAAGATGTG | AAGCCTCTGT | CTCACTGAGG | ATTTTAAAGG | 2591 |
| TCAATTATAC | TTTTGTTGTT | CATTAGCATC | TTTGTAAACT | ATAAGACGTA | GTTTTAATTA | 2651 |
| ATAAATATTG | CCCCCAGATG | TTAAAAAAAA | AAAAAAAA | | | 2690 |

( 2 ) INFORMATION FOR SEQ ID NO:12:

( i ) SEQUENCE CHARACTERISTICS:

( A ) LENGTH: 772 amino acids
( B ) TYPE: amino acid
( D ) TOPOLOGY: linear ( i i ) MOLECULE TYPE: protein ( x i ) SEQUENCE DESCRIPTION: SEQ ID NO:12:

| Met | Ala | Ala | Glu | Ser | Ala | Leu | Gln | Val | Val | Glu | Lys | Leu | Gln | Ala | Arg |
|---|---|---|---|---|---|---|---|---|---|---|---|---|---|---|---|
| 1 | | | | 5 | | | | | 10 | | | | | 15 | |

| Leu | Ala | Ala | Asn | Pro | Asp | Pro | Lys | Lys | Leu | Leu | Lys | Tyr | Leu | Lys | Lys |
|---|---|---|---|---|---|---|---|---|---|---|---|---|---|---|---|
| | | | 20 | | | | 25 | | | | | 30 | | | |

| Leu | Ser | Thr | Leu | Pro | Ile | Thr | Val | Asp | Ile | Leu | Ala | Glu | Thr | Gly | Val |
|---|---|---|---|---|---|---|---|---|---|---|---|---|---|---|---|
| | | 35 | | | | 40 | | | | | 45 | | | | |

| Gly | Lys | Thr | Val | Asn | Ser | Leu | Arg | Lys | His | Glu | His | Val | Gly | Ser | Phe |
|---|---|---|---|---|---|---|---|---|---|---|---|---|---|---|---|
| | 50 | | | | | 55 | | | | | 60 | | | | |

| Ala | Arg | Asp | Leu | Val | Ala | Gln | Trp | Lys | Lys | Leu | Val | Pro | Val | Glu | Arg |
|---|---|---|---|---|---|---|---|---|---|---|---|---|---|---|---|
| 65 | | | | | 70 | | | | 75 | | | | | | 80 |

| Asn | Ala | Glu | Pro | Asp | Glu | Gln | Asp | Phe | Glu | Lys | Ser | Asn | Ser | Arg | Lys |
|---|---|---|---|---|---|---|---|---|---|---|---|---|---|---|---|
| | | | | 85 | | | | | 90 | | | | | 95 | |

| Arg | Pro | Arg | Asp | Ala | Leu | Gln | Lys | Glu | Glu | Met | Glu | Gly | Asp | Tyr |
|---|---|---|---|---|---|---|---|---|---|---|---|---|---|---|
| | | | 100 | | | | | 105 | | | | 110 | | |

| Gln | Glu | Thr | Trp | Lys | Ala | Thr | Gly | Ser | Arg | Ser | Tyr | Ser | Pro | Asp | His |
|---|---|---|---|---|---|---|---|---|---|---|---|---|---|---|---|
| | | 115 | | | | | 120 | | | | | 125 | | | |

| Arg | Gln | Lys | Lys | His | Arg | Lys | Leu | Ser | Glu | Leu | Glu | Arg | Pro | His | Lys |
|---|---|---|---|---|---|---|---|---|---|---|---|---|---|---|---|
| | 130 | | | | | 135 | | | | | 140 | | | | |

| Val | Ser | His | Gly | His | Glu | Arg | Arg | Asp | Glu | Arg | Lys | Arg | Cys | His | Arg |
|---|---|---|---|---|---|---|---|---|---|---|---|---|---|---|---|
| 145 | | | | | 150 | | | | 155 | | | | | | 160 |

| Met | Ser | Pro | Thr | Tyr | Ser | Ser | Asp | Pro | Glu | Ser | Ser | Asp | Tyr | Gly | His |
|---|---|---|---|---|---|---|---|---|---|---|---|---|---|---|---|
| | | | | 165 | | | | | 170 | | | | | 175 | |

| Val | Gln | Ser | Pro | Pro | Ser | Cys | Thr | Ser | Pro | His | Gln | Met | Tyr | Val | Asp |
|---|---|---|---|---|---|---|---|---|---|---|---|---|---|---|---|
| | | | 180 | | | | | 185 | | | | | 190 | | |

| His | Tyr | Arg | Ser | Leu | Glu | Glu | Asp | Gln | Glu | Pro | Ile | Val | Ser | His | Gln |
|---|---|---|---|---|---|---|---|---|---|---|---|---|---|---|---|
| | | 195 | | | | | 200 | | | | | 205 | | | |

| Lys | Pro | Gly | Lys | Gly | His | Ser | Asn | Ala | Phe | Gln | Asp | Arg | Leu | Gly | Ala |
|---|---|---|---|---|---|---|---|---|---|---|---|---|---|---|---|
| | 210 | | | | | 215 | | | | | 220 | | | | |

| Ser | Gln | Glu | Arg | His | Leu | Gly | Glu | Pro | His | Gly | Lys | Gly | Val | Val | Ser |
|---|---|---|---|---|---|---|---|---|---|---|---|---|---|---|---|
| 225 | | | | | 230 | | | | 235 | | | | | | 240 |

| Gln | Asn | Lys | Glu | His | Lys | Ser | Ser | His | Lys | Asp | Lys | Arg | Pro | Val | Asp |
|---|---|---|---|---|---|---|---|---|---|---|---|---|---|---|---|
| | | | | 245 | | | | | 250 | | | | | 255 | |

| Ala | Lys | Ser | Asp | Glu | Lys | Ala | Ser | Val | Val | Ser | Arg | Glu | Lys | Ser | His |
|---|---|---|---|---|---|---|---|---|---|---|---|---|---|---|---|
| | | | 260 | | | | | 265 | | | | | 270 | | |

| Lys | Ala | Leu | Ser | Lys | Glu | Glu | Asn | Arg | Arg | Pro | Pro | Ser | Gly | Asp | Asn |
|---|---|---|---|---|---|---|---|---|---|---|---|---|---|---|---|
| | | | 275 | | | | 280 | | | | | 285 | | | |

| Ala | Arg | Glu | Lys | Pro | Pro | Ser | Ser | Gly | Val | Lys | Lys | Glu | Lys | Asp | Arg |
|---|---|---|---|---|---|---|---|---|---|---|---|---|---|---|---|
| | 290 | | | | | 295 | | | | | 300 | | | | |

| Glu | Gly | Ser | Ser | Leu | Lys | Lys | Cys | Leu | Pro | Pro | Ser | Glu | Ala | Ala |
|---|---|---|---|---|---|---|---|---|---|---|---|---|---|---|
| 305 | | | | | 310 | | | | 315 | | | | | 320 |

| Ser | Asp | Asn | His | Leu | Lys | Lys | Pro | Lys | His | Arg | Asp | Pro | Glu | Lys | Ala |
|---|---|---|---|---|---|---|---|---|---|---|---|---|---|---|---|
| | | | | 325 | | | | | 330 | | | | | 335 | |

| Lys | Leu | Asp | Lys | Ser | Lys | Gln | Gly | Leu | Asp | Ser | Phe | Asp | Thr | Gly | Lys |
|---|---|---|---|---|---|---|---|---|---|---|---|---|---|---|---|
| | | | 340 | | | | | 345 | | | | | 350 | | |

| Gly | Ala | Gly | Asp | Leu | Leu | Pro | Lys | Val | Lys | Glu | Lys | Gly | Ser | Asn | Asn |
|---|---|---|---|---|---|---|---|---|---|---|---|---|---|---|---|
| | | 355 | | | | 360 | | | | | 365 | | | | |

| Leu | Lys | Thr | Pro | Glu | Gly | Lys | Val | Lys | Thr | Asn | Leu | Asp | Arg | Lys | Ser |
|---|---|---|---|---|---|---|---|---|---|---|---|---|---|---|---|
| 370 | | | | | 375 | | | | | 380 | | | | | |

| | | | | | | | | | | | | | |
|---|---|---|---|---|---|---|---|---|---|---|---|---|---|
| Leu | Gly | Ser | Leu | Pro | Lys | Val | Glu | Thr | Asp | Met | Glu | Asp | Phe |
| 385 | | | | | 390 | | | | 395 | | | | 400 |
| Glu | Gln | Pro | Thr | Met | Ser | Phe | Glu | Ser | Tyr | Leu | Ser | Tyr | Asp | Gln | Pro |
| | | | | 405 | | | | | 410 | | | | | 415 |
| Arg | Lys | Lys | Lys | Lys | Ile | Val | Lys | Thr | Ser | Ala | Thr | Ala | Leu | Gly |
| | | | 420 | | | | 425 | | | | 430 | | | |
| Asp | Lys | Gly | Leu | Lys | Lys | Asn | Asp | Ser | Lys | Ser | Thr | Gly | Lys | Asn | Leu |
| | | 435 | | | | 440 | | | | | 445 | | | |
| Asp | Ser | Val | Gln | Lys | Leu | Pro | Lys | Val | Asn | Lys | Thr | Lys | Ser | Glu | Lys |
| | 450 | | | | | 455 | | | | | 460 | | | | |
| Pro | Ala | Gly | Ala | Asp | Leu | Ala | Lys | Leu | Arg | Lys | Val | Pro | Asp | Val | Leu |
| 465 | | | | | 470 | | | | | 475 | | | | | 480 |
| Pro | Val | Leu | Pro | Asp | Leu | Pro | Leu | Pro | Ala | Ile | Gln | Ala | Asn | Tyr | Arg |
| | | | | 485 | | | | | 490 | | | | | 495 | |
| Pro | Leu | Pro | Ser | Leu | Glu | Leu | Ile | Ser | Ser | Phe | Gln | Pro | Lys | Arg | Lys |
| | | | 500 | | | | | 505 | | | | | 510 | | |
| Ala | Phe | Ser | Ser | Pro | Gln | Glu | Glu | Glu | Ala | Gly | Phe | Thr | Gly | Arg |
| | | 515 | | | | 520 | | | | | 525 | | | |
| Arg | Met | Asn | Ser | Lys | Met | Gln | Val | Tyr | Ser | Gly | Ser | Lys | Cys | Ala | Tyr |
| | 530 | | | | | 535 | | | | | 540 | | | | |
| Leu | Pro | Lys | Met | Met | Thr | Leu | His | Gln | Gln | Cys | Ile | Arg | Val | Leu | Lys |
| 545 | | | | | 550 | | | | | 555 | | | | | 560 |
| Asn | Asn | Ile | Asp | Ser | Ile | Phe | Glu | Val | Gly | Gly | Val | Pro | Tyr | Ser | Val |
| | | | | 565 | | | | | 570 | | | | | 575 | |
| Leu | Glu | Pro | Val | Leu | Glu | Arg | Cys | Thr | Pro | Asp | Gln | Leu | Tyr | Arg | Ile |
| | | | 580 | | | | | 585 | | | | | 590 | | |
| Glu | Glu | Tyr | Asn | His | Val | Leu | Ile | Glu | Glu | Thr | Asp | Gln | Leu | Trp | Lys |
| | | 595 | | | | | 600 | | | | | 605 | | | |
| Val | His | Cys | His | Arg | Asp | Phe | Lys | Glu | Glu | Arg | Pro | Glu | Glu | Tyr | Glu |
| | 610 | | | | | 615 | | | | | 620 | | | | |
| Ser | Trp | Arg | Glu | Met | Tyr | Leu | Arg | Leu | Gln | Asp | Ala | Arg | Glu | Gln | Arg |
| 625 | | | | | 630 | | | | | 635 | | | | | 640 |
| Leu | Arg | Val | Leu | Thr | Lys | Asn | Ile | Gln | Phe | Ala | His | Ala | Asn | Lys | Pro |
| | | | | 645 | | | | | 650 | | | | | 655 | |
| Lys | Gly | Arg | Gln | Ala | Lys | Met | Ala | Phe | Val | Asn | Ser | Val | Ala | Lys | Pro |
| | | | 660 | | | | | 665 | | | | | 670 | | |
| Pro | Arg | Asp | Val | Arg | Arg | Arg | Gln | Glu | Lys | Phe | Gly | Thr | Gly | Gly | Ala |
| | | 675 | | | | | 680 | | | | | 685 | | | |
| Ala | Val | Pro | Glu | Lys | Ile | Lys | Ile | Lys | Pro | Ala | Pro | Tyr | Pro | Met | Gly |
| | 690 | | | | | 695 | | | | | 700 | | | | |
| Ser | Ser | His | Ala | Ser | Ala | Ser | Ser | Ile | Ser | Phe | Asn | Pro | Ser | Pro | Glu |
| 705 | | | | | 710 | | | | | 715 | | | | | 720 |
| Glu | Pro | Ala | Tyr | Asp | Gly | Pro | Ser | Thr | Ser | Ser | Ala | His | Leu | Ala | Pro |
| | | | | 725 | | | | | 730 | | | | | 735 | |
| Val | Val | Ser | Ser | Thr | Val | Ser | Tyr | Asp | Pro | Arg | Lys | Pro | Thr | Val | Lys |
| | | | 740 | | | | | 745 | | | | | 750 | | |
| Lys | Ile | Ala | Pro | Met | Met | Ala | Lys | Thr | Ile | Lys | Ala | Phe | Lys | Asn | Arg |
| | | 755 | | | | | 760 | | | | | 765 | | | |
| Phe | Ser | Arg | Arg |
| | 770 | | |

( 2 ) INFORMATION FOR SEQ ID NO:13:

( i ) SEQUENCE CHARACTERISTICS:
        ( A ) LENGTH: 13 amino acids (B) TYPE: amino acid
(C) STRANDEDNESS:
(D) TOPOLOGY: linear (ii) MOLECULE TYPE: peptide (xi) SEQUENCE DESCRIPTION: SEQ ID NO:13:

Leu Ile Ser Ser Asp Gly His Glu Phe Ile Val Lys Arg
1               5                   10

(2) INFORMATION FOR SEQ ID NO:14:

(i) SEQUENCE CHARACTERISTICS:
(A) LENGTH: 20 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:14:

Ala Met Leu Ser Gly Pro Gly Gln Phe Ala Glu Asn Glu Thr Asn Glu
1               5                   10                  15

Val Asn Phe Arg
            20

(2) INFORMATION FOR SEQ ID NO:15:

(i) SEQUENCE CHARACTERISTICS:
(A) LENGTH: 8 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:15:

Val Cys Met Tyr Phe Thr Tyr Lys
1               5

(2) INFORMATION FOR SEQ ID NO:16:

(i) SEQUENCE CHARACTERISTICS:
(A) LENGTH: 29 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:16:

Tyr Thr Asn Ser Ser Thr Glu Ile Pro Glu Phe Pro Ile Ala Pro Glu
1               5                   10                  15

Ile Ala Leu Glu Leu Leu Met Ala Ala Asn Phe Leu Asp
            20                  25

(2) INFORMATION FOR SEQ ID NO:17:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: misc_feature
(B) LOCATION: 1..20
(D) OTHER INFORMATION: /note= "degenerate oligonucleotide"

( x i ) SEQUENCE DESCRIPTION: SEQ ID NO:17:

CARTTYGCNG ARAAYGARAC 20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..20
        ( D ) OTHER INFORMATION: /note= "degenerate oligonucleotide"

( x i ) SEQUENCE DESCRIPTION: SEQ ID NO:18:

GGNGCDATNG GRAAYTCNGG 20

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..20
        ( D ) OTHER INFORMATION: /note= "degenerate oligonucleotide"

( x i ) SEQUENCE DESCRIPTION: SEQ ID NO:19:

ACNAAYGARG TNAAYTTYMG 20

( 2 ) INFORMATION FOR SEQ ID NO:20:

( i ) SEQUENCE CHARACTERISTICS:
        ( A ) LENGTH: 29 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:20:

Leu Tyr Lys Asp Asp Gln Leu Leu Asp Asp Gly Lys Thr Leu Gly Glu
1               5                   10                  15

Cys Gly Phe Thr Ser Gln Thr Ala Arg Pro Gln Ala Pro
            20                  25

( 2 ) INFORMATION FOR SEQ ID NO:21:

( i ) SEQUENCE CHARACTERISTICS:
        ( A ) LENGTH: 34 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:21:

Ala Asp Asp Thr Gly Glu Ala Leu Arg Ile Glu Pro Phe Ser Ser Pro
1               5                   10                  15

```
          Pro  Glu  Leu  Pro  Asp  Val  Met  Lys  Pro  Gln  Asp  Ser  Gly  Gly  Ser  Ala
                         20                       25                       30

Asn  Glu
```

( 2 ) INFORMATION FOR SEQ ID NO:22:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..19
        ( D ) OTHER INFORMATION: /note= "degenerate oligonucleotide"

( x i ) SEQUENCE DESCRIPTION: SEQ ID NO:22:

```
TNTAYAARGA  YGAYCARYT                                                                    19
```

( 2 ) INFORMATION FOR SEQ ID NO:23:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..20
        ( D ) OTHER INFORMATION: /note= "degenerate oligonucleotide"

( x i ) SEQUENCE DESCRIPTION: SEQ ID NO:23:

```
TGNGGYTTCA  TNACRTCNGG                                                                   20
```

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..20
        ( D ) OTHER INFORMATION: /note= "degenerate oligonucleotide"

( x i ) SEQUENCE DESCRIPTION: SEQ ID NO:24:

```
GCNGAYGAYA  CNTTYGARGC                                                                   20
```

( 2 ) INFORMATION FOR SEQ ID NO:25:

( i ) SEQUENCE CHARACTERISTICS:
        ( A ) LENGTH: 30 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:25:

```
          Asp  Val  Pro  Gln  Gln  Glu  Glu  Glu  Ala  Glu  Gly  Asn  Tyr  Gln  Glu  Ser
          1                    5                        10                      15
```

```
            Trp  Gln  Ala  Ser  Gly  Ser  Gln  Pro  Tyr  Tyr  Pro  Glu  His  Arg
                      20                      25                      30
```

(2) INFORMATION FOR SEQ ID NO:26:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:26:

```
Ala  Asn  Glu  Asn  Lys  Ser  Asp  Lys  Leu  Gln  Pro  Ala  Gly  Ala  Glu  Pro
 1              5                        10                       15

Thr  Arg  Pro
```

(2) INFORMATION FOR SEQ ID NO:27:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: modified_base
        (B) LOCATION: 12
        (D) OTHER INFORMATION: /mod_base=i (ix) FEATURE:
        (A) NAME/KEY: modified_base
        (B) LOCATION: 17
        (D) OTHER INFORMATION: /mod_base=i (ix) FEATURE:
        (A) NAME/KEY: modified_base
        (B) LOCATION: 35
        (D) OTHER INFORMATION: /mod_base=i (ix) FEATURE:
        (A) NAME/KEY: modified_base
        (B) LOCATION: 38
        (D) OTHER INFORMATION: /mod_base=i (xi) SEQUENCE DESCRIPTION: SEQ ID NO:27:

```
TCCTGGTAGT TNCCTCNGCC TCCTCCTCCT GCTGNGGNAC GTC                    43
```

(2) INFORMATION FOR SEQ ID NO:28:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: modified_base
        (B) LOCATION: 9
        (D) OTHER INFORMATION: /mod_base=i (ix) FEATURE:
        (A) NAME/KEY: modified_base
        (B) LOCATION: 15
        (D) OTHER INFORMATION: /mod_base=i (ix) FEATURE:
        (A) NAME/KEY: modified_base (B) LOCATION: 18
(D) OTHER INFORMATION: /mod_base=i (ix) FEATURE:
(A) NAME/KEY: modified_base
(B) LOCATION: 21
(D) OTHER INFORMATION: /mod_base=i (ix) FEATURE:
(A) NAME/KEY: modified_base
(B) LOCATION: 24
(D) OTHER INFORMATION: /mod_base=i (xi) SEQUENCE DESCRIPTION: SEQ ID NO:28:

CGGATCGTNG GYTCNGCNCC NGCNGGYTG    29

(2) INFORMATION FOR SEQ ID NO:29:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:29:

CGTAATACGA CTCACTATAG GG    22

(2) INFORMATION FOR SEQ ID NO:30:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:30:

Met His His His His His His Asn Val Asp
1               5                   10

(2) INFORMATION FOR SEQ ID NO:31:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:31:

Met His His His His His His Asn Val Asp
1               5                   10

(2) INFORMATION FOR SEQ ID NO:32:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:32:

GCAGCGGATC CTCAACAATC TAGGAAGTTC G    31

( 2 ) INFORMATION FOR SEQ ID NO:33:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

GCAACGTCGA CATGGACGTG TTTCTCATGA T        31

( 2 ) INFORMATION FOR SEQ ID NO:34:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

GCAGCGGATC CTCACTGCAC AGCTTGTTCA T        31

( 2 ) INFORMATION FOR SEQ ID NO:35:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

GCNGAYGAYA CNTTYGARGC        20

( 2 ) INFORMATION FOR SEQ ID NO:36:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

GCTTTCTCCC TTGCATTGTC CC        22

( 2 ) INFORMATION FOR SEQ ID NO:37:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

CCTCTAGAAT TTCTCTCTGC TCACCACAGG        30